US008247374B2

(12) United States Patent
Anversa

(10) Patent No.: US 8,247,374 B2
(45) Date of Patent: Aug. 21, 2012

(54) METHODS AND COMPOSITIONS FOR THE REPAIR AND/OR REGENERATION OF DAMAGED MYOCARDIUM USING CYTOKINES AND VARIANTS THEREOF

(75) Inventor: Piero Anversa, Boston, MA (US)

(73) Assignee: New York Medical College, Valhalla, NY (US)

( * ) Notice: Subject to any disclaimer, the term of this patent is extended or adjusted under 35 U.S.C. 154(b) by 691 days.

(21) Appl. No.: 12/267,849

(22) Filed: Nov. 10, 2008

(65) Prior Publication Data

US 2009/0157046 A1 Jun. 18, 2009

Related U.S. Application Data

(60) Provisional application No. 60/986,788, filed on Nov. 9, 2007.

(51) Int. Cl.
*A61K 38/18* (2006.01)
*A61K 38/30* (2006.01)
*C07K 14/475* (2006.01)
(52) U.S. Cl. ............ 514/9.5; 514/7.6; 514/8.6; 435/377
(58) Field of Classification Search .................. None
See application file for complete search history.

(56) References Cited

U.S. PATENT DOCUMENTS

| 5,197,985 | A | 3/1993 | Caplan et al. |
|---|---|---|---|
| 5,199,942 | A | 4/1993 | Gillis |
| 5,202,120 | A | 4/1993 | Silver et al. |
| 5,543,318 | A | 8/1996 | Smith et al. |
| 5,580,779 | A | 12/1996 | Smith et al. |
| 5,602,301 | A | 2/1997 | Field |
| 5,833,975 | A | 11/1998 | Paoletti et al. |
| 5,906,934 | A | 5/1999 | Grande et al. |
| 5,908,782 | A | 6/1999 | Marshak et al. |
| 5,942,235 | A | 8/1999 | Paoletti |
| 5,990,091 | A | 11/1999 | Tartaglia et al. |
| 6,001,934 | A | 12/1999 | Yamanaka et al. |
| 6,004,777 | A | 12/1999 | Tartaglia et al. |
| 6,036,972 | A | 3/2000 | Nakamura et al. |
| 6,099,832 | A | 8/2000 | Mickle et al. |
| 6,110,459 | A | 8/2000 | Mickle et al. |
| 6,117,675 | A | 9/2000 | Van der Kooy et al. |
| 6,130,066 | A | 10/2000 | Tartaglia et al. |
| 6,174,333 | B1 | 1/2001 | Kadiyala et al. |
| 6,255,292 | B1 | 7/2001 | Liang |
| 6,265,189 | B1 | 7/2001 | Paoletti et al. |
| 6,329,348 | B1 | 12/2001 | Crystal et al. |
| 6,387,369 | B1 | 5/2002 | Pittenger et al. |
| 6,547,787 | B1 | 4/2003 | Altman et al. |
| 7,179,786 | B2 | 2/2007 | Gherardi et al. |
| 7,547,674 | B2 * | 6/2009 | Anversa et al. ............ 514/1.1 |
| 8,008,254 | B2 * | 8/2011 | Anversa ....................... 514/8.6 |
| 2002/0122792 | A1 | 9/2002 | Stegmann |
| 2003/0054973 | A1 | 3/2003 | Anversa |
| 2003/0105015 | A1 | 6/2003 | Gilbertson et al. |
| 2004/0258669 | A1 | 12/2004 | Dzau et al. |
| 2005/0037431 | A1 | 2/2005 | Kirchhofer et al. |
| 2006/0239983 | A1 | 10/2006 | Anversa |
| 2009/0143296 | A1 | 6/2009 | Anversa |
| 2009/0148421 | A1 | 6/2009 | Anversa et al. |
| 2009/0162329 | A1 | 6/2009 | Anversa et al. |
| 2009/0169525 | A1 | 7/2009 | Anversa et al. |
| 2009/0180998 | A1 | 7/2009 | Anversa et al. |

FOREIGN PATENT DOCUMENTS

| JP | 11-246433 | 9/1999 |
|---|---|---|
| WO | WO 92/11865 | 7/1992 |
| WO | WO 95/12979 | 5/1995 |
| WO | WO 95/14079 | 5/1995 |
| WO | WO 95/28174 | 10/1995 |
| WO | WO 95/34581 | 12/1995 |
| WO | WO 96/04314 | 2/1996 |
| WO | WO 96/38544 | 12/1996 |
| WO | WO 98/51798 A | 11/1998 |
| WO | WO 99/45775 | 9/1999 |
| WO | WO 00/06701 | 2/2000 |
| WO | WO 00/57922 | 10/2000 |
| WO | WO 01/026694 | 4/2001 |
| WO | WO 01/034179 | 5/2001 |
| WO | WO 01/094420 | 12/2001 |
| WO | WO 02/02593 A | 1/2002 |
| WO | WO 02/088354 A | 11/2002 |
| WO | WO 2007/058776 A | 5/2007 |
| WO | WO 2007/100530 A | 9/2007 |

OTHER PUBLICATIONS

Huang, Jul-Han et al. "Protein Transfer of Preformed MHC-Peptide Complexes Sensitizes Target Cells to T Cell Cytolysis," *Immunity*, vol. 1: 607-613, Oct. 1994.
Ross, Russell, "The pathogenesis of atherosclerosis: a perspective for the 1990s," Nature, vol. 362: 801-809, Apr. 1993.
Sensebe, Luc, et al., The Broad Spectrum of Cytokine Gene Expression by Myoid Cells from the Human Marrow Microenvironment, *Stem Cells*, vol. 15: 133-143, Nov. 2, 1997.
Wartiovaara, Ulla, et al., "Peripheral Blood Platelets Express VEGF-C and VEGF which are Released during Platelet Activation," *Thromb Haemost*, vol. 80: 171-175, 1998.
Mohle, Robert, et al., "Constitutive production and thrombin-induced release of vascular endothelial growth factor by human megakaryocytes and platelets," *Proc. Natl. Acad. Sci. USA*, vol. 94: 663-668, Jan. 21, 1997.

(Continued)

*Primary Examiner* — Daniel C Gamett
(74) *Attorney, Agent, or Firm* — Cooley LLP

(57) ABSTRACT

Methods, compositions, and kits for repairing damaged myocardium and/or myocardial cells including the administration of cytokines, variants of cytokines, cardiac stem cells, or combinations thereof are disclosed and claimed. In addition, methods, compositions, and kits for forming coronary vasculature including the administration of cytokines, variants of cytokines, cardiac stem cells, or combinations thereof are described. In particular, administration of variants of hepatocyte growth factor, such as NK1, 1K1, and HP11, are useful for the repair and/or regeneration of damaged myocardium or formation of coronary vasculature. Methods of activating cardiac stem cells in vitro are also disclosed.

27 Claims, 2 Drawing Sheets

OTHER PUBLICATIONS

Boyden, Stephen, "The Chemotactic Effect of Mixtures of Antibody and Antigen on Polymorphonuclear Leucocytes," *J. Exptl. Med.* vol. 115: 453-456, 1962.

American Heart Association. 2001 Heart and Stroke Statistical Update. Dallas, Texas: American Heart Association, 2000.

Bautz, F. et al., "Expression and secretion of vascular endothelial growth factor-A by cytokine stimulated hematopoietic progenitor cells. Possible role in the hernatopoietic microenvironment." *Exp Hematol*, vol. 28(6):700-706, Jun. 2000.

Beardsle, M. A. et al., "Rapid turnover of connexin43 in the adult rat heart." *Circ. Res.* vol. 83: 629-635, 1998.

Beltrami, C.A. et al., "Structural basis of end-stage failure in ischemic cardiomyopathy in humans." *Circulation* vol. 89: 151-163, 1994.

Bianco, P. et al. "Bone marrow stromal stem cells: nature, biology, and potential applications." *Stem Cells* vol. 19:180-192, 2001.

Blume et al., "A review of autologous hematopoietic cell transplantation." *Biology of Blood & Marrow Transplantation*, vol. 6: 1-12, 2000.

Bodine, D.M. et al., "Efficient retrovirus transduction of mouse pluripotent hematopoietic stem cells mobilized into the peripheral blood by treatment with granulocyte colony-stimulating factor and stem cell factor." *Blood*, vol. 84: 1482-1491, 1994.

Breier, G. et al., "Molecular cloning and expression of murine vascular endothelial-cadherin in early stage development of cardiovascular system." *Blood*, vol. 87: 630-641, 1996.

Brugger et al., "Ex vivo manipulation of hematopoietic stem and progenitor cells." *Seminars in Hematology*, vol. 37 (1): 42-49, 2000.

Caceres-Cortes, J.R. et al., "Steel factor sustains SCL expression and the survival of purified CD34+ bone marrow cells in the absence of detectable cell differentiation." *Stem Cells* vol. 19(1):59-70, Jan. 2001.

Chiu et al., "Cellular Cardiomyoplasty: Mycardial Regeneration With Satellite Cell Implantation." *Ann. Thorac. Surg.*, vol. 60: 12-18, 1995.

Clutterbuck, R.D. et al., "G-CSF mobilization of haemopoietic cell populations in SCID mice engrafted with human leukaernia." *Bone Marrow Transplant*, vol. 20(4):325-332, Aug. 1997.

Couper, L.L. et al., "Vascular endothelial growth factor increases the mitogenic response to fibroblast growth factor-2 in vascular smooth muscle cells in vivo via expression of fms-like tyrosine kinase-1." *Circ. Res.*, vol. 81: 932-939, 1997.

Durocher, D. et al., "The cardiac transcription factors Nkx2-5 and GATA-4 are mutual cofactors." *EMBO J.*, vol. 16: 5687-5696, 1997.

Fielding et al., "Autologous bone marrow transplantation." *Curr. Opin. Hematology*, vol. 1: 412-417, 1994.

Gussoni et al., "Normal dystrophin transcripts detected in Duchenne muscular dystrophy patients after myoblast transplantation." *Nature*, vol. 356:435-438, 1992.

Hermann, H. and Aebi, U. "In Subcellular Biochemistry: Intermediate Filaments." vol. 31 (ed. Henmann, H. & Harris, E.): 319-362 (Plenum Press, New York, 1998).

Huang H.M. et al., "Optimal proliferation of a hematopoietic progenitor cell line requires either costitnulation with stem cell factor or increase of receptor expression that can be replaced by over expression of Bcl-2." *Blood*, vol. 93(8):2569-2577, Apr. 1999.

Ikuta, K. et al., "Mouse hematopoietic stem cells and the interaction of c-kit receptor and steel factor." *International Journal of Cell Cloning*, vol. 9:451-460, 1991.

Janowska-Wieczorek, A. et al., "Autocrine/paracrine mechanisms in human hematopoiesis." *Stem Cells*, vol. 19:99-107, 2001.

Jo, D.Y. et al., "Chemotaxis of primitive hematopoietic cells in response to stromal cell-derived factor-1." *The Journal of Clinical Investigation*, vol. 105(1): 101-111, Jan. 2000.

Kachinsky, A.M. et al., "Intermediate filaments in cardiac myogenesis: nestin in the developing mouse heart." *J. Histochem. Cytochem.*, vol. 43: 843-847, 1995.

Kanj et al., "Myocardial ischemia associated with high-dose carmustine infusion.", *Cancer*, vol. 68 (9):1910-1912, 1991.

Kajstura, J. et al., "The cellular basis of pacing-induced dilated cardiomyopathy. Myocyte cell loss and myocyte cellular reactive hypertrophy." *Circulation*, vol. 92: 2306-2317, 1995.

Kasahara, H. et al., "Cardiac and extracardiac expression of Csx/Nkx2.5 homeodomain protein." *Circ. Res.*, vol. 82: 936-946, 1998.

Keil F. et al., "Effect of interleukin-3, stem cell factor and granulocyte-macrophage colony-stimulating factor on committed stem cells: long-term culture initiating cells and bone marrow stroma in a one-step long-term bone marrow culture." *Ann. Hematol.*, vol. 79(5):243-248, May 2000.

Kempermann, G. et al., "Activity-dependent regulation of neuronal plasticity and self repair." *Prog Brain Res.*, vol. 127:35-48, 2000.

Kim, C.H. and Broxmeyer H.E., "In vitro behavior of hematopoietic progenitor cells under the influence of chemoattractants: stromal cell-derived factor-1, steel factor, and the bone marrow environment." *Blood*, vol. 91(1):100-110, Jan. 1998.

Koh et al., "Differentiation and long-term survival of C2C12 myoblast grafts in heart." *Journal of Clinical Investigation*, vol. 92: 1548-1554, 1993.

Krause, D.S. et al., "Multi-organ, multi-lineage engraftment by a single bone marrow-derived stem cell." *Cell*, vol. 105(3): 369-370, May 2001.

Kronenwett, R. et al., "The role of cytokines and adhesion molecules for mobilization of peripheral blood stem cells." *Stem Cells*, vol. 18:320-330, 2000.

Laiuppa, J.A. et al., "Evaluation of cytokines for expansion of the megakaryocyte and granulocyte lineages." *Stem Cells*, vol. 15(3): 198-206, May 1997.

Leor et al., "Transplantation of Fetal Myocardial Tissue Into the Infarcted Myocardium of Rat, A Potential Method for Repair of Infarcted Myocardium?" *Circulation*, vol. 94:(Supplement II) II-332-II-336, 1996.

Li et al., "Method of Culturing Cardiomyocytes from Human Pediatric Ventricular Myocardium." *J. Tiss. Cult. Meth.*, vol. 14: 93-100, 1992.

Li, Q. et al. "Overexpression of insulin-like growth factor-1 in mice protects from myocyte death after infarction, attenuating ventricular dilation, wall stress, and cardiac hypertrophy." *J Clin Invest.*, vol. 100: 1991-1999, 1997.

Li, B et al., "Insulin-like growth factor-1 attenuates the detrimental impact of nonocclusive coronary artery constriction on the heart." *Circ. Res.* vol. 84: 1007-1019, 1999.

Li et al., "Human Pediatric and Adult Ventricular Cardiomyocytes in Culture: Assessment of Phenotypic Changes with Passaging." *Cardiovascular Res.*, vol. 32:362-373, 1996.

Li et al., "In Vivo Survival and Function of Transplanted Rat Cardiomyocytes" *Circulation Research*, vol. 78:283-288, 1996.

Li et al., "Cardiomyocyte Transplantation Improves Heart Function." *The Society of Thoracic Surgeons*, vol. 62: 654-661, 1996.

Lin, Q. et al., "Control of mouse cardiac morphogenesis and myogenesis by transcription factor MEF2C." *Science*, vol. 276: 1404-1407, 1997.

Malouf, N.N. et al., "Adult derived stem cells from the liver become myocytes in the heart in vivo." *Am J Pathology*, vol. 158(6):1929-1935, Jun. 2001.

Menasche, P. et al., "Myoblast Transplantation for Heart Failure." *Lancet*, vol. 357: 279-280, 2000.

Morin, S. et al., "GATA-dependent recruitment of MEF2 proteins to target promoters." *EMBO J.*, vol. 19: 2046-2055, 2000.

Murray et al., "Skeletal Myoblast Transplantation for Repair of Myocardial Necrosis" *J. Clin. Invest.*, vol. 98:2512-2523, 1996.

Musil, L. S. et al., "Regulation of connexin degradation as a mechanism to increase gap junction assembly and function." *J. Biol. Chem.*, vol. 275: 25207-25215, 2000.

National Institutes of Health. "Stem Cells : A Primer." National Insitutes of Health: May 2000.

Noishiki et al., "Angiogenic growth factor release system for in vivo tissue engineering: a trial of bone marrow transplantation into ischemic myocardium." *J. Artif. Organs*, vol. 2: 85-91, 1999.

Olivetti, G. et al., "Cellular basis of chronic ventricular remodeling after myocardial infarction in rats." *Circ. Res.*, vol. 68(3): 856-869, 1991.

Orlic, D. et al., "Identification of Human and Mouse Hematopoietic Stem Cell Populations Expressing High Levels of mRNA Encoding Retrovirus Receptors." *Blood*, vol. 91: 3247-3254, 1998.
Orlic, D. et al., "Bone marrow cells regenerate infarcted myocardium." Nature, vol. 410: 701-705, 2001.
Patchen, ML et al. "Mobilization of peripheral blood progenitor cells by Betafectin® PGG-glucan alone and in combination with granulocyte colony-stimulating factor." *Stem Cells*, vol. 16(3):208-217, May 1998.
Pfeffer, M. A. and Braunwald, E. "Ventricular remodeling after myocardial infarction." *Circulation*, vol. 81:1161-1172, 1990.
Pollick, C. et al., "Echocardiographic and cardiac Doppler assessment of mice." *J. Am. Soc. Echocardiogr.*, vol. 8: 602-6 10, 1995.
Reiss, K. et al., "Overexpression of insulin-like growth factor-1 in the heart is coupled with myocyte proliferation in transgenic mice." *Proc. Natl. Acad. Sci. USA*, vol. 93(16): 8630-8635, 1996.
Roberts M.M., et al., "Prolonged release and c-kit expression of haemopoietic precursor cells mobilized by stem cell factor and granulocyte colony stimulating factor." *Br J Haematol.*, vol. 104(4):778-784, Mar. 1999.
Rosenthal, N. and Tsao, L. "Helping the heart to heal with stem cells." *Nature Medicine*, vol. 7(4):412-413, Apr. 2001.
Scholzen, T., and Gerdes, J. "The ki-67 protein: from the known and the unknown." *J. Cell. Physiol.*, vol. 182: 311-322, 2000.
Shimomura T., et al., "Thrombopoietin stimulates murine lineage negative, Sca-1+, C-Kit+, CD34-cells: comparative study with stem cell factor or interleukin-3." *Int J Hematol.*, vol. 71(1): 33-39, Jan. 2000.
Soonpaa et al. "Formation of nascent intercalated disks between grafted fetal cardiomyocytes and host myocardium." Science, vol. 264(5155):98-101, 1994.
Simnett et al. "Autologous stem cell transplantation for malignancy: a systemic review of the literature." *Clin. Lab Haem.*, vol. 22:61-72, 2000.
Strobel, ES et al. "Adhesion and migration are differentially regulated in hematopoietic progenitor cells by cytokines and extracellular matrix." *Blood*, vol. 90(9):3524-3532, Nov. 1997.
Taylor, D.A. et al., "Regenerating Functional Myocardium: Improved Performance After Skeletal Myoblast Transplantation." *Nature Medicine*, vol. 4: 929-933, 1998.
Temple, S. "Opinion: Stem cell plasticity—building the brain of our dreams." *Nat Rev Neurosci.*, vol. 2(7): 513-520, Jul. 2001.
Thompson et al., "Fetal Transplants Show Promise." *Science*, vol. 257:868-870, 1992.
Tomita, S et al. "Autologous Transplantation of Bone Marrow Cells Improves Damaged Heart Function." *Circulation*, vol. 100(suppl II):II-247-II-256, 1999.
Vaughn et al. "Incorporating bone marrow transplantation into NCCN guidelines." *Oncology*, vol. 12 (11A): 390-392, 1998.
Yamaguchi, T.P. et al., "Flk-1, an flt-related receptor tyrosine kinase is an early marker for endothelial cell precursors. Development." *Development*, vol. 118(2): 489-498, 1993.
Quaini, F. et al. "Chimerism of the human heart: role of stem cells." *Abstract*, 2001.
Anversa, P. and Nadal-Ginard, B., "Myocyte renewal and ventricular remodelling." *Nature*, vol. 415(6868):240-243,2002.
Quaini, F. et al., "Chimerism of the transplanted heart." *N Engl J Med.*, vol. 346(1):5-15, 2002.
Reya, T. et al., "Stem cells, cancer, and cancer stem cells." *Nature*, vol. 414(6859):105-111, 2001.
Jackson, K.A. et al., "Hematopoietic potential of stem cells isolated from murine skeletal muscle." *Proc Natl Acad Sci USA.*, vol. 96(25): 14482-14486, 1999.
Orlic, D. et al., "Mobilized bone marrow cells repair the infarcted heart, improving function and survival." *Proc Natl Acad Sci USA.*, vol. 98(18): 10344-10349, 2001.
Blau, H.M. et al., "The evolving concept of a stem cell: entity or function?" *Cell*, vol. 105(7):829-41, 2001.
Monga, S.P.S. et al. "Expansion of hepatic and hematopoietic stem cells utilizing mouse embryonic liver explants." *Cell Transplant*, vol. 10(1): 81-89, 2001.
Weimar, I.S. et al., "Hepatocyte growth factor/scatter factor (HGF/SF) is produced by human bone marrow stromal cells and promotes proliferation, adhesion and survival of human hernatopoietic progenitor cells (CD34+)." *Exp Hematol.*, vol. 26(9):885-94, 1998.
Yu, C.Z. et al., "Stimulatory Effects of Hepatocyte Growth Factor on Hemopoiesis of SCF/c-kit System Deficient Mice." *Stem Cells*, vol. 16, 66-77, 1998.
Birchmeier, C. and Brohmann, H., "Genes that Control the Development of Migrating Muscle Precursor Cells." *Curr. Opin. Cell Biol.*, vol. 12: 725-730, 2001.
Xin, X. et al., "Hepatocyte Growth Factor Enhances Vascular Endothelial Growth Factor-Induced Angiogenesis in Vitro and in Vivo." *Am. J. Pathol.*, vol. 158:1111-1120, 2001.
Hamasuna, R. et al. "Regulation of matrix metalloproteinase-2 (MMP-2) by hepatocyte growth factor/scatter factor (HGF/SF) in human glioma cells: HGF/SF enhances MMP-2 expression and activation accompanying up-regulation of membrane type-1 MMP." *Int J Cancer*, vol. 82(2):274-281, 1999.
Wang, H. and Keiser, J.A., "Hepatocyte growth factor enhances MMP activity in human endothelial cells." *Biochem Biophys Res Commun.*, vol. 272(3):900-905, 2000.
Arsenijevic, Y. et al., "Insulin-like growth factor-1 is necessary for neural stem cell proliferation and demonstrates distinct actions of epidermal growth factor and fibroblast growth factor-2." *J Neurosci.*, vol. 21(18):7194-7202, 2001.
Arsenijevic, Y. and Weiss, S., "Insulin-like growth factor-I is a differentiation factor for postmitotic CNS stem cell-derived neuronal precursors: distinct actions from those of brain-derived neurotrophic factor." *J Neurosci.*, vol. 18(6):2118-2128, 1998.
Brooker, G.J. et al., "Endogenous IGF-1 regulates the neuronal differentiation of adult stem cells." *J Neurosci Res.*, vol. 59(3):332-341, 2000.
Page, D.L. et al., "Myocardial changes associated with cardiogenic shock." *N Engl J Med.*, vol. 285(3): 133-137, 1971.
Pasumarthi, K.B.S. et al., "Coexpression of mutant p53 and p193 renders embryonic stem cell-derived cardiomyocytes responsive to the growth-promoting activities of adenoviral E1A." *Circ Res.*, vol. 88(10): 1004-1011, 2001.
Condorelli, G. et al., "Cardiomyocytes induce endothelial cells to trans-differentiate into cardiac muscle: implications for myocardium regeneration." *Proc Natl Acad Sci USA.*, vol. 98(19): 10733-10738, 2001.
Beltrami, A.P. et al. "Evidence that human cardiac myocytes divide after myocardial infarction." *N Engl J Med.*, vol. 344(23): 1750-1757, 2001.
Jackson, K.A. et al., "Regeneration of Ischemic Cardiac Muscle and Vascular Endothelium by Adult Stem Cells." J. Clin. Invest., vol. 107: 1395-1402, 2001.
Maclellan, W.R. and Schneider, M.D. "Genetic dissection of cardiac growth control pathways." *Annu. Rev. Physiol.*, vol. 62:289-319, 2000.
Hidemasa, 0. et al. "Telomerase reverse transcriptase promotes cardiac muscle cell proliferation, hypertrophy, and survival." *Proc. Natl. Acad. Sci. USA*, vol. 98:10308-10313, 2001.
Anversa, P. and Kajstura, J. "Ventricular myocytes are not terminally differentiated in the adult mammalian heart." *Circ. Res.*, vol. 83:1-14, 1998.
Rao, MS. and Mattson, M.P. Stem cells and aging: expanding the possibilities. *Mech. Ageing Dev.*, vol. 122:713-734, 1998.
Zaucha, J.M. et al. "Hematopoietic responses to stress conditions in young dogs compared with elderly dogs." *Blood*, vol. 98: 322-327, 2001.
Gritti, A. et al. "Epidermal and fibroblast growth factors behave as mitogenic regulators for a single multipotent stem cell-like population from the subventricular region of the adult mouse forebrain." *J. Neurosci.*, vol. 19:3287-3297, 1999.
Shihabuddin, L.S. et al., "Adult spinal cord stem cells generate neurons after transplantation in the adult dentate gyrus." *J. Neurosci.*, vol. 20: 8727-8735, 2000.
Cheng, W. et al. "Aging does not affect the activation of the myocyte IGF-1 autocrine system after infarction and ventricular failure in Fischer 344 rats." *Circ. Res.*, vol. 78: 536-546, 1996.
Kajstura, J. et al. "Apoptotic and necrotic myocyte cell deaths are independent contributing variables of infarct size in rats." *Lab. Invest.*, vol. 74: 86-107, 1996.

Mikawa, T. & Fishman, D.A. "The polyclonal origin of myocyte lineages." *Annu. Rev. Physiol.*, vol. 58: 509-521, 1996.

Stainer, D.Y.R. et al., "Cardiovascular development in zebrafish. I. Myocardial fate and heart tube formation." *Development*, vol. 119:31-40, 1993.

Hillebrands, J-L. et al. "Origin of neointimal endothelium and α-actin-positive smooth muscle cells in transplant arteriosclerosis." *J. Clin. Invest.*, vol. 107: 1411-1422, 2001.

Eisenberg, C.A & Bader, D. "QCE-6: a clonal cell line with cardiac myogenic and endothelial cell potentials." *Dev. Biol.*, vol. 167: 469-481, 1995.

Kehat, I. et al. "Human embryonic stem cells can differentiate into myocytes with structural and functional properties of myocytes." *J. Clin. Invest.*, vol. 108: 407-414, 2001.

Anderson, D.J. "Stem cells and pattern formation in the nervous system: the possible versus the actual." *Neuron*, vol. 30: 19-35, 2001.

Lee, J.Y. et al. "Clonal isolation of muscle-derived cells capable of enhancing muscle regeneration and bone healing." *J. Cell Biol.*, vol. 150: 1085-1099, 2000.

Seale, P. et al. "Pax7 is required for the specification of myogenic satellite cells." *Cell*, vol. 102: 777-786, 2000.

Broudy, V.C. "Stem cell factor and hematopoiesis." *Blood*, vol. 90: 1345-1364, 1997.

Tropepe, V. et al. "Distinct neural stem cells proliferate in response to EGF and FGF developing mouse telencephalon." *Dev. Biol.*, vol. 208: 166-188, 1999.

Li, P. et. al. "Myocyte performance during evolution of myocardial infarction in rats: effects of propionyl-L-carnitine." *Am. J, Physiol.*, vol. 208: H1702-H1713, 1995.

Bunting, K.D. et al., "Enforced P-Glycoprotein Pump Function in Murine Bone Marrow Cells Results in Expansion of Side Population Stem Cells in Vitro and Repopulating Cells in Vivo." *Blood*, vol. 96: 902-909, 2000.

Block, G.D. et al., "Population Expansion, Clonal Growth, and Specific Differentiation Patterns in Primary Cultures of Hepatocytes Induced by HGF/SF, EGF, and TGFα in a Chemically Defined (HGM) Medium." J. Cell Biol., vol. 132: 1133-1149, 1996.

Rappolee, D.A. et al., "Hepatocyte Growth Factor and Its Receptor Are Expressed in Cardiac Myocytes During Early Cardiogenesis." *Circ. Res.*, vol. 78: 1028-1036, 1996.

Powell, E.M. et al., "Hepatocyte Growth Factor/Scatter Factor is a Motogen for Interneurons Migrating from the Ventral to Dorsal Telencephalon." *Neuron*, vol. 30: 79-89, 2001.

Leri, A. et al., "Overexpression of Insulin-Like Growth Factor-1 Attenuates the Myocyte Renin-Angiotensin System in Transgenic Mice." *Circ. Res.*, vol. 84: 752-762, 1999.

Capasso, J.M. and Anversa, P., "Mechanical Performance of Spared Myocytes After Myocardial Infarction in Rats: Effects of Captopril Treatment." *Am. J. Physiol.*, vol. 263: H841-H849, 1992.

Taylor et al., "Cardiac Chimerism as a Mechanism for Self-Repair: Does it Happen and If So to What Degree?" Circulation, vol. 106(1): 2-4, Jul. 2002.

Foley et al., "Heart Induction: Embryology to Cardiomyocyte Regeneration." Trends Cardiovasc. Med., vol. 14(3):121-125, Apr. 2004.

Nagai et al., "Promotion of Cardiac Regeneration by Cardiac Stem Cells." Circulation Research, vol. 97: 615-617, 2005.

Kanellakis et al. "Granulocyte-colony Stimulating Factor and Stem Cell Factor Improve Endogenous Repair After Myocardial Infarction." Circulation Research, vol. 70: 117-125, 2006.

Deten et al. "Hematopoietic Stem Cells Do Not Repair the Infarcted Mouse Heart." Cardiovascular Research, vol. 65: 52-63, 2005.

Yasuda et al. "Single Low Dose Administration of Human Recombinant Hepatocyte Growth Factor Attenuates Intimal Hyperplasia in a Balloon-Injured Rabbit Iliac Artery Model." Circulation, vol. 101: 2546-2549, May 2000.

Norol et al. "Influence of Mobilized Stem Cells on Myocardial Infarct Repair in a Nonhuman Primate Model." Blood, vol. 102:4361-4368, 2003.

Ohtsuka et al. "Cytokine Therapy Prevents Left Ventricular Remodeling and Dysfunction After Myocardial Infarction Through Neovascularization." FASEB, vol. 18:851-853, 2004.

Orlic et al. "Cytokine Mobilized CD34+ Cells Do Not Benefit Rhesus Monkeys Following Induced Myocardial Infarction." Blood, vol. 100(11): 28a-29a, 2002.

Mohri et al., "Leukemia inhibitory factor induces endothelial differentiation in cardiac stem cells." Journal of Biological Chemistry, vol. 281: 6442-6447, 2006d.

Young et al., "Mesenchymal Stem Cells Reside Within the Connective Tissues of Many Organs." *Developmental Dynamics* 1995, vol. 202 pp. 137-144.

Nakamura et al., "Myocardial protection from ischemia/reperfusion injury by endogenous and exogenous HGF." *J. Clin. Invest.* 2000, vol. 106, pp. 1511-1519.

Yamamura et al., "IGF-I differentially regulates Bcl-xL and Bax and confers myocardial protection in the rat heart." *Am. J. Physiol. Heart Circ. Physiol.* 2001, vol. 280, pp. H1191-H1200.

Segers et al., "Stem-cell therapy for cardiac disease." *Nature* 2008, vol. 451, pp. 937-942.

"Insulin-Transerrin-Sodium Selenite Supplement," Online Datasheet, Roche Diagnostics. 2005, retrieved on Sep. 7, 2008 from internet URL: http://roche-applied-science.com/pack-insert/1074547a.pdf.

Saitou et al., "Occludin-deficient embryonic stem cells can differentiate into polarized epithelial cells bearing tight junctions." Journal of Cell Biology, 1998, vol. 141, pp. 397-408.

Urbanek et al., "Cardiac stem cells possess growth factor-receptor systems that after activation regenerate the infarcted myocardium, improving ventricular function and long-term survival", *Circulation Research*, Sep. 2005, 97(7):663-673.

Linke et al., "Stem cells in the dog heart are self-renewing, clonogenic, and multipotent and regenerate infarcted myocardium, improving cardiac function", *Proceedings of the National Academy of Science*, 102(25): 8966-8971.

Fey-Lamprecht, International Search Report based on International Application No. PCT/US2008/082967 (May 11, 2009).

* cited by examiner

A

B

METHODS AND COMPOSITIONS FOR THE REPAIR AND/OR REGENERATION OF DAMAGED MYOCARDIUM USING CYTOKINES AND VARIANTS THEREOF

CROSS REFERENCE TO RELATED APPLICATIONS

This application claims the benefit of U.S. Provisional Application No. 60/986,788, filed Nov. 9, 2007, which is herein incorporated by reference in its entirety.

STATEMENT OF GOVERNMENT SUPPORT

This work was in part supported by the government, by grants from the National Institutes of Health, Grant Nos: HL-38132, AG-15756, HL-65577, HL-55757, HL-68088, HL-70897, HL-76794, HL-66923, HL65573, HL-075480, AG-17042, HL-081737, AG-026107 and AG-023071. The government may have certain rights to this invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: AUTL_002_01US_SeqList_ST25.txt, date recorded: Jan. 29, 2009, file size 22 kilobytes).

FIELD OF THE INVENTION

The present invention relates generally to the field of cardiology, and more particularly relates to methods and cellular compositions for treatment of a patient suffering from a cardiovascular disease, including, but not limited to, atherosclerosis, ischemia, hypertension, restenosis, angina pectoris, rheumatic heart disease, congenital cardiovascular defects and arterial inflammation and other disease of the arteries, arterioles and capillaries. The present invention contemplates treatments, therapeutics and methodologies that can be used in place of, or in conjunction with, traditional, invasive therapeutic treatments such as cardiac or vascular bypass surgery.

BACKGROUND OF THE INVENTION

Cardiovascular disease is a major health risk throughout the industrialized world. Atherosclerosis, the most prevalent of cardiovascular diseases, is the principal cause of heart attack, stroke, and gangrene of the extremities, and thereby the principal cause of death in the United States. Atherosclerosis is a complex disease involving many cell types and molecular factors (for a detailed review, see Ross, 1993, Nature 362: 801-809).

Ischemia is a condition characterized by a lack of oxygen supply in tissues of organs due to inadequate perfusion. Such inadequate perfusion can have number of natural causes, including atherosclerotic or restenotic lesions, anemia, or stroke, to name a few. Many medical interventions, such as the interruption of the flow of blood during bypass surgery, for example, also lead to ischemia. In addition to sometimes being caused by diseased cardiovascular tissue, ischemia may sometimes affect cardiovascular tissue, such as in ischemic heart disease. Ischemia may occur in any organ, however, that is suffering a lack of oxygen supply.

The most common cause of ischemia in the heart is myocardial infarction (MI), commonly known as a heart attack, is one of the most well-known types of cardiovascular disease. 1998 estimates show 7.3 million people in the United States suffer from MI, with over one million experiencing an MI in a given year (American Heart Association, 2000). Of these individuals, 25% of men, and 38% of females will die within a year of their first recognized MI (American Heart Association, 2000). MI is caused by a sudden and sustained lack of blood flow to an area of the heart, commonly caused by narrowing of a coronary artery. Without adequate blood supply, the tissue becomes ischemic, leading to the death of myocytes and vascular structures. This area of necrotic tissue is referred to as the infarct site, and will eventually become scar tissue. Survival is dependent on the size of this infarct site, with the probability of recovery decreasing with increasing infarct size. For example, in humans, an infarct of 46% or more of the left ventricle triggers irreversible cardiogenic shock and death (99).

Current treatments for MI focus on reperfusion therapy, which attempts to start the flow of blood to the affected area to prevent the further loss of tissue. The main choices for reperfusion therapy include the use of anti-thrombolytic agents, or performing balloon angioplasty, or a coronary artery bypass graft. Anti-thrombolytic agents solubilize blood clots that may be blocking the artery, while balloon angioplasty threads a catheter into the artery to the site of the occlusion, where the tip of the catheter is inflated, pushing open the artery. Still more invasive procedures include the bypass, where surgeons remove a section of a vein from the patient, and use it to create a new artery in the heart, which bypasses the blockage, and continues the supply of blood to the affected area. In 1998, there were an estimated 553,000 coronary artery bypass graft surgeries and 539,000 percutaneous transluminal coronary angioplastys. These procedures average $27,091 and $8,982 per patient, respectively (American Heart Association, 2000).

These treatments may succeed in reestablishing the blood supply, however tissue damage that occurred before the reperfusion treatment began has been thought to be irreversible. For this reason, eligible MI patients are started on reperfusion therapy as soon as possible to limit the area of the infarct.

As such, most studies on MI have also focused on reducing infarct size. There have been a few attempts to regenerate the necrotic tissue by transplanting cardiomyocytes or skeletal myoblasts (Leor et al., 1996; Murray, et al., 1996; Taylor, et al., 1998; Tomita et al., 1999; Menasche et al., 2000). While the cells may survive after transplantation, they fail to reconstitute healthy myocardium and coronary vessels that are both functionally and structurally sound.

All of the cells in the normal adult originate as precursor cells which reside in various sections of the body. These cells, in turn, derive from very immature cells, called progenitors, which are assayed by their development into contiguous colonies of cells in 1-3 week cultures in semisolid media such as methylcellulose or agar. Progenitor cells themselves derive from a class of progenitor cells called stem cells. Stem cells have the capacity, upon division, for both self-renewal and differentiation into progenitors. Thus, dividing stem cells generate both additional primitive stem cells and somewhat more differentiated progenitor cells. In addition to the well-known role of stem cells in the development of blood cells, stem cells also give rise to cells found in other tissues, including but not limited to the liver, brain, and heart.

Stem cells have the ability to divide indefinitely, and to specialize into specific types of cells. Totipotent stem cells, which exist after an egg is fertilized and begins dividing, have total potential, and are able to become any type of cell. Once the cells have reached the blastula stage, the potential of the cells has lessened, with the cells still able to develop into any cell within the body, however they are unable to develop into the support tissues needed for development of an embryo. The cells are considered pluripotent, as they may still develop into many types of cells. During development, these cells become more specialized, committing to give rise to cells with a specific function. These cells, considered multipotent, are found in human adults and referred to as adult stem cells. It is well known that stem cells are located in the bone marrow, and that there is a small amount of peripheral blood stem cells that circulate throughout the blood stream (National Institutes of Health, 2000).

Due to the regenerative properties of stem cells, they have been considered an untapped resource for potential engineering of tissues and organs. It would be an advance to provide uses of stem cells with respect to addressing cardiac conditions.

Mention is made of:

U.S. Pat. No. 6,117,675 which relates to the differentiation of retinal stem cells into retinal cells in vivo or in vitro, which can be used as a therapy to restore vision.

U.S. Pat. No. 6,001,934 involving the development of functional islets from islets of Langerhans stem cells.

U.S. Pat. Nos. 5,906,934 and 6,174,333 pertaining to the use of mesenchymal stem cells for cartilage repair, and the use of mesenchymal stem cells for regeneration of ligaments; for instance, wherein the stem cells are embedded in a gel matrix, which is contracted and then implanted to replace the desired soft tissue.

U.S. Pat. Nos. 6,099,832, and 6,110,459 involving grafts with cell transplantation.

PCT Application Nos. PCT/US00/08353 (WO 00/57922) and PCT/US99/17326 (WO 00/06701) involving intramyocardial injection of autologous bone marrow and mesenchymal stem cells which fails to teach or suggest administering, implanting, depositing or the use of hematopoietic or cardiac stem cells as in the present invention, especially as the hematopoietic and cardiac stem cells as in the present invention are advantageously isolated and/or purified adult hematopoietic or cardiac stem cells.

Only recent literature has started to investigate the potentials for stem cells to aid in the repair of tissues other than that of known specialization. This plasticity of stem cells, the ability to cross the border of germ layers, is a concept only in its infancy (Kempermann et al, 2000, Temple, 2001). Kocher et al (2001) discusses the use of adult bone marrow to induce neovascularization after infarction as an alternative therapy for left ventricle remodeling (reviewed in Rosenthal and Tsao, 2001). Other studies have focused on coaxing specific types of stem cells to differentiate into myocardial cells, e.g. liver stem cells as shown in Malour et al. (2001). Still other work focuses on the possibilities of bone-marrow derived stem cells (Krause, et al., 2001).

One of the oldest uses of stem cells in medicine is for the treatment of cancer. In these treatments, bone marrow is transplanted into a patient whose own marrow has been destroyed by radiation, allowing the stem cells in the transplanted bone marrow to produce new, healthy, white blood cells.

In these treatments, the stem cells are transplanted into their normal environment, where they continue to function as normal. Until recently, it was thought that any particular stem cell line was only capable of producing three or four types of cells, and as such, they were only utilized in treatments where the stem cell was required to become one of the types of cells for which their ability was already proven. Researchers are beginning to explore other options for treatments of myriad disorders, where the role of the stem cell is not well defined.

Organ transplantation has been widely used to replace diseased, nonfunctional tissue. More recently, cellular transplantation to augment deficiencies in host tissue function has emerged as a potential therapeutic paradigm. One example of this approach is the well publicized use of fetal tissue in individuals with Parkinsonism (reviewed in Tompson, 1992), where dopamine secretion from transplanted cells alleviates the deficiency in patients. In other studies, transplanted myoblasts from unaffected siblings fused with endogenous myotubes in Duchenne's patients; importantly the grafted myotubes expressed wild-type dystrophin (Gussoni et al., 1992).

Despite their relevance in other areas, these earlier studies do not describe any cellular transplantation technology that can be successfully applied to the heart, where the ability to replace damaged myocardium would have obvious clinical relevance. Additionally, the use of intra-cardiac grafts to target the long-term expression of angiogenic factors and ionotropic peptides would be of therapeutic value for individuals with myocardial ischemia or congestive heart failure, respectively.

In light of this background there is a need for the improvement of myocardial regeneration technology in the heart. Desirably, such technology would not only result in tissue regeneration in the heart but also enable the delivery of useful compositions directly to the heart. The present invention addresses these needs.

SUMMARY OF THE INVENTION

The present invention is based, in part, on the discovery that cardiac stem cells reside in the heart and these stem cells can be mobilized by cytokines to areas of damaged myocardial tissue. Upon migration to the damaged tissue, cardiac stem cells differentiate into myocytes, endothelial cells and smooth muscle cells and proliferate to form structures including myocardium, coronary arteries, arterioles, and capillaries, thereby restoring the structural and functional integrity of the damaged tissue.

It has surprisingly been found that hepatocyte growth factor and in particular, variants of hepatocyte growth factor, are particularly useful for mobilizing adult cardiac stem cells in vivo. Accordingly, the present invention provides a method for restoring functional and structural integrity to damaged myocardium in a subject in need thereof. In one embodiment, the method comprises administering to the subject an effective amount of at least one variant of hepatocyte growth factor to form a chemotactic gradient in the subject's heart sufficient to cause adult cardiac stem cells resident in the heart to replicate and migrate to the area of the damaged myocardium, wherein the functional and structural integrity of the damaged myocardium is restored following the migration of adult cardiac stem cells to the area of damaged myocardium. The variant of hepatocyte growth factor may include natural splice variants, truncations of the full-length protein, and/or mutations of the protein, such as NK1, 1K1, 1K2, HP11, and HP21.

In some embodiments, the method further comprises administering a second cytokine, wherein the second cytokine induces proliferation of adult cardiac stem cells. In one embodiment, the second cytokine is insulin-like growth factor-1.

In another embodiment, the invention provides methods and/or compositions for repairing and/or regenerating recently damaged myocardium and/or myocardial cells comprising the administration of an effective amount of one or more cytokines, e.g. hepatocyte growth factor, insulin-like growth factor-1 or variants thereof for causing the migration and/or proliferation of cardiac stem cells or cardiac primative cells into circulatory tissue or muscle tissue or circulatory muscle tissue. This migration and/or proliferation is advantageously employed in the treatment or therapy or prevention of cardiac conditions, such as to treat areas of weakness or scarring in the heart or prevent the occurrence or further occurrence of such areas or to treat conditions which cause or irritate such areas, for instance myocardial infarction or ischemia or other conditions (e.g. genetic) that impart weakness or scarring to the heart. In a preferred embodiment, a variant of hepatocyte growth factor is administered intramyocardially to cause the migration of resident cardiac stem cells to damaged tissue and effect repair. In another preferred embodiment, said variant of hepatocyte growth factor is NK1.

The invention also provides methods and/or compositions for forming coronary vasculature in an infracted portion of the ventricular wall comprising administering to the subject an effective amount of at least one variant of hepatocyte growth factor to form a chemotactic gradient in the subject's heart sufficient to cause adult cardiac stem cells resident in the heart to replicate and migrate to the area of the infarction, wherein vasculogenesis forms coronary vasculature in the infarcted portion of the ventricular wall following the migration of adult cardiac stem cells to the infarcted portion.

The invention also encompasses growth media that can be used in the culture and expansion of adult cardiac stem cells, in particular human cardiac stem cells. Also provided is growth media that can be used to activate cardiac stem cells, in particular human cardiac stem cells. Cardiac stem cells grown in said media can be administered to regenerate myocardium or vasculature. Activated stem cells grown in the media can also be administered to regenerate myocardium or vasculature, wherein vasculature includes large arteries and veins, such as in a biological bypass.

The present invention also provides a method of adult cardiac stem cells. In one embodiment, the method comprises incubating isolated adult cardiac stem cells in a solution comprising at least one cytokine, wherein the at least one cytokine is a variant of hepatocyte growth factor. Suitable variants of hepatocyte growth factor include NK1, 1K1, 1K2, HP11, and HP21. In a preferred embodiment, said variant of hepatocyte growth factor is NK1. In another embodiment, the solution for activating adult cardiac stem cells may further comprise a second cytokine, wherein the second cytokine induces proliferation of adult cardiac stem cells. In yet another embodiment, said second cytokine is insulin-like growth factor-1.

The invention also provides methods and/or compositions for forming coronary vessels or arteries in a patient in need thereof comprising administering activated cardiac stem cells to the location in which a vessel or artery is desired. The cardiac stem cells may be isolated and activated by exposing the cardiac stem cells to one or more variants of hepatocyte growth factor including HP11, NK1, and 1K1. These methods can potentially generate a biological bypass of an occluded or obstructed artery to allow for reperfusion of the ischemic tissue. Such methods can be used in place of, or in conjunction with, traditional methods of cardiac bypass surgery.

The invention provides methods and/or compositions for repairing and/or regenerating recently damaged myocardium and/or myocardial cells comprising the administration of somatic stem cells, e.g., adult stem cells or cardiac stem cells or hematopoietic stem cells or a combination thereof, such as adult cardiac or adult hematopoietic stem cells or a combination thereof or a combination of cardiac stem cells and a stem cell of another type, such as a combination of adult cardiac stem cells and adult stem cells of another type. In one embodiment, the invention provides media for use in the culturing and/or expansion of stem cells in vitro, prior to the administration of the stem cells. In another embodiment, said media includes one or more variants of hepatocyte growth factor to activate the stem cells prior to administration.

The invention further provides methods and/or compositions for repairing and/or regenerating recently damaged myocardium and/or myocardial cells comprising the administration of at least one cytokine or variant thereof in combination with a pharmaceutical agent useful in the treatment of cardiac or vascular conditions.

The present invention also encompasses a method for restoring structural and functional integrity to damaged myocardium in a subject in need thereof comprising extracting cardiac stem cells from the subject; culturing and expanding said cardiac stem cells; activating the extracted and expanded cardiac stem cells by exposing the cardiac stem cells to at least one variant of hepatocyte growth factor; and administering an effective dose of said activated cardiac stem cells to an area of damaged myocardium in the subject, wherein the activated cardiac stem cells restore structural and functional integrity to the damaged myocardium following their administration. In one embodiment, extracting cardiac stem cells from the subject comprises harvesting myocardial tissue from the subject and isolating the cardiac stem cells from said myocardial tissue. In another embodiment, the activated cardiac stem cells are administered intracoronarily. In some embodiments, the activated cardiac stem cells differentiate into myocytes, smooth muscle cells, and endothelial cells following their administration and form myocardial tissue and coronary vessels.

The invention still further relates to a method and/or compositions for repairing and/or regenerating recently damaged myocardium comprising the administration of somatic stem cells, e.g., adult stem cells or cardiac stem cells or hematopoietic stem cells or a combination thereof, such as adult cardiac or adult hematopoietic stem cells or a combination thereof or a combination of cardiac stem cells and a stem cell of another type, such as a combination of adult cardiac stem cells and adult stem cells of another type and a cytokine or variant thereof.

The invention yet further provides a method for preparing any of the aforementioned or herein disclosed compositions comprising admixing the pharmaceutically acceptable carrier and the somatic stem cells and/or cytokines or cytokine variants.

The invention provides methods involving implanting, depositing, administering or causing the implanting or depositing or administering of stem cells, such as adult stem cells, for instance hematopoietic or cardiac stem cells or a combination thereof or any combination of cardiac stem cells (e.g., adult cardiac stem cells) and stem cells of another type (e.g., adult stem cells of another type), alone or with a cytokine such as a cytokine selected from the group consisting of hepatocyte growth factor, variants of hepatocyte growth factor including HP11, HP21, NK1, 1K1, and 1K2, insulin growth factor-1, or any cytokine capable of the stimulating and/or mobilizing stem cells (wherein "with a cytokine..." can include sequential implanting, depositing administering or causing of implanting or depositing or administering of the stem cells and the cytokine or the co-implanting co-depositing or co-administering or causing of co-implanting or co-depositing or co-administering or the simultaneous implanting, depositing administering or causing of implanting or depositing or administering of the stem cells and the cytokine), in circulatory tissue or muscle tissue or circulatory muscle tissue, e.g., cardiac tissue, such as the heart or blood vessels—e.g., veins, arteries, that go to or come from the heart such as veins and arteries directly connected or attached or flowing into the heart, for instance the aorta. This implanting, depositing, or administering or causing of implanting, depositing or administering can be in conjunction with grafts.

Such implanting, depositing or administering or causing of implanting, depositing or administering is advantageously employed in the treatment or therapy or prevention of cardiac conditions, such as to treat areas of weakness or scarring in the heart or prevent the occurrence or further occurrence of such areas or to treat conditions which cause or irritate such areas, for instance myocardial infarction or ischemia or other e.g., genetic, conditions that impart weakness or scarring to the heart (see also cardiac conditions mentioned supra).

The invention additionally provides the use of such stem cells alone or in combination with said cytokine(s) or variants thereof, in the formulation of medicaments for such treatment, therapy or prevention.

And thus, the invention also provides medicaments for use in such treatment, therapy or prevention comprising the stem cells and optionally the cytokine(s).

Likewise the invention provides kits comprising the stem cells and optionally the cytokine(s) or variants thereof for formulations for use in such treatment, therapy or prevention. The stem cells and the cytokine(s) can be in separate containers in a package or in one container in a package; and, the kit can optionally include a device for administration (e.g., syringe, catheter, etc.) and/or instructions for administration and/or admixture.

The invention also provides compositions comprising such stem cells and optionally the cytokine(s) or cytokine variants and kits for preparing such compositions as well as methods of making the aforementioned compositions.

The invention also provides a means of generating and/or regenerating myocardium ex vivo, wherein somatic stem cells and heart tissue are cultured in vitro, optionally in the presence of a cytokine or cytokine variant. The somatic stem cells differentiate into myocytes, smooth muscle cells and endothelial cells, and proliferate in vitro, forming myocardial tissue and/or cells. These tissues and cells may assemble into cardiac structures including arteries, arterioles, capillaries, and myocardium. The tissue and/or cells formed in vitro may then be implanted into a patient, e.g. via a graft, to restore structural and functional integrity.

DETAILED DESCRIPTION OF THE INVENTION

Figure 1:
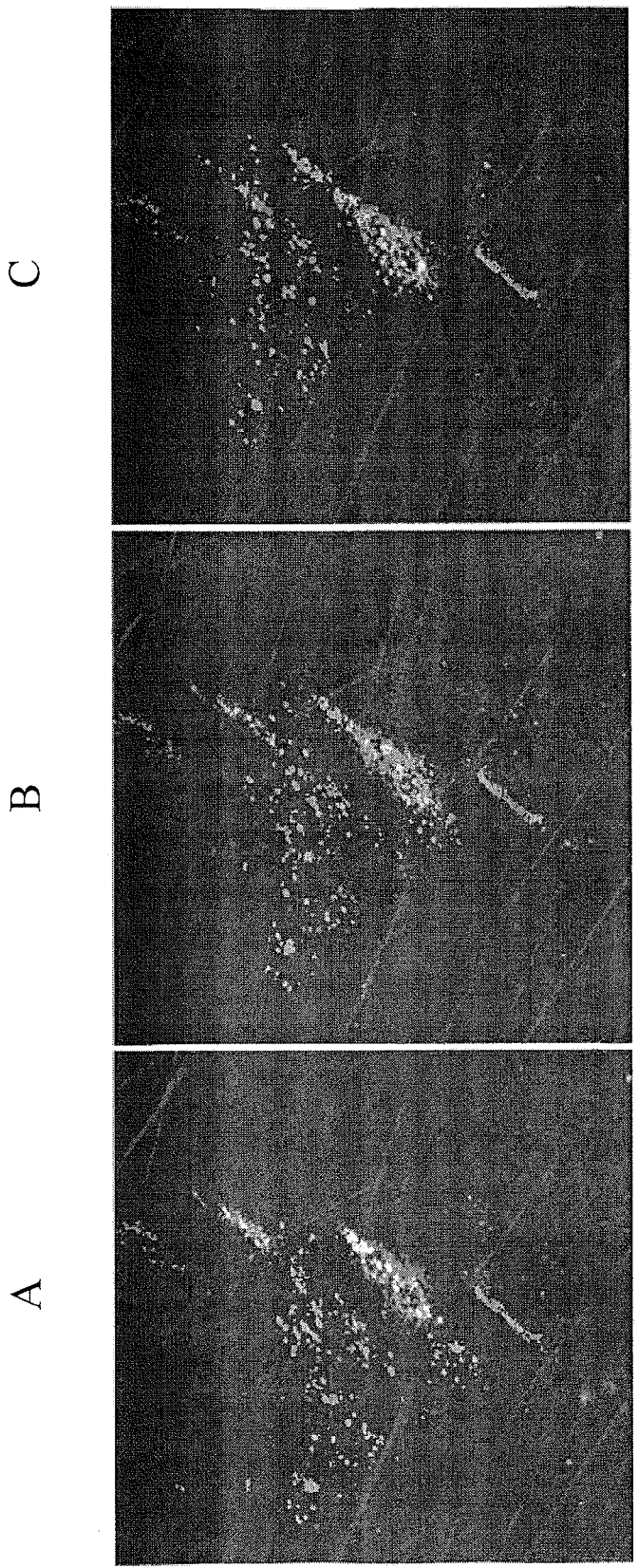
FIG. 1. Migration of implanted human cardiac stem cells activated with NK1 and IGF-1 to infarct site in a mouse model of myocardial infarction. EGFP$^{POS}$-c-kit$^{POS}$-cardiac stem cells (CSCs) were activated prior to implantation with NK1 and IGF-1. The three different panels show the migration of the EGFP$^{POS}$ stem cells over time (A, B, and C represent time points: 0, 1 hour and 2 hours, respectively). Red label=rhodamine-labeled microspheres co-injected with the human CSCs to mark the sites of injection. Green label=implanted human CSCs expressing EGFP. Blue label=collagen fibers.

As used herein "somatic stem cell" or "stem cell" refers to either autologous or allogenic stem cells, which may be obtained from the bone marrow, peripheral blood, or other source (e.g. heart).

As used herein, "autologous" refers to something that is derived or transferred from the same individual's body (i.e., autologous blood donation; an autologous bone marrow transplant).

As used herein, "allogenic" refers to something that is genetically different although belonging to or obtained from the same species (e.g., allogeneic tissue grafts).

As used herein, "adult" stem cells refers to stem cells that are not embryonic in origin nor derived from embryos or fetal tissue.

Stem cells employed in the invention are advantageously selected to be lineage negative. The term "lineage negative" is known to one skilled in the art as meaning the cell does not express antigens characteristic of specific cell lineages. And, it is advantageous that the lineage negative stem cells are selected to be c-kit positive. The term "c-kit" is known to one skilled in the art as being a receptor which is known to be present on the surface of stem cells, and which is routinely utilized in the process of identifying and separating stem cells from other surrounding cells.

As used herein "recently damaged myocardium" refers to myocardium which has been damaged within one week of treatment being started. In a preferred embodiment, the myocardium has been damaged within three days of the start of treatment. In a further preferred embodiment, the myocardium has been damaged within 12 hours of the start of treatment. It is advantageous to employ stem cells alone or in combination with cytokines or variants thereof as herein disclosed to a recently damaged myocardium.

As used herein "damaged myocardium" refers to myocardial cells which have been exposed to ischemic conditions. These ischemic conditions may be caused by a myocardial infarction, or other cardiovascular disease or related complaint. The lack of oxygen causes the death of the cells in the surrounding area, leaving an infarct, which will eventually scar.

As used herein, "home" refers to the attraction and mobilization of somatic stem cells towards damaged myocardium and/or myocardial cells.

As used herein, "assemble" refers to the assembly of differentiated somatic stem cells into functional structures, e.g. myocardium and/or myocardial cells, coronary arteries, arterioles, and capillaries etc. This assembly provides functionality to the differentiated myocardium and/or myocardial cells, coronary arteries, arterioles and capillaries.

As used herein, the term "cytokine" is used interchangeably with "growth factor" and refers to peptides or proteins that bind receptors on cell surfaces and initiate signaling cascades thus influencing cellular processes. The terms "cytokine" and "growth factor" encompass functional variants of the native cytokine or growth factor. A functional variant of the cytokine or growth factor would retain the ability to activate its corresponding receptor. Variants can include amino acid substitutions, insertions, deletions, alternative splice variants, or fragments of the native protein. The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological activity can be found using computer programs well known in the art, for example, DNASTAR software.

The pharmaceutical compositions of the present invention may be used as therapeutic agents—i.e. in therapy applications. As used herein, the terms "treatment" and "therapy" include curative effects, alleviation effects, and prophylactic effects. In certain embodiments, a therapeutically effective dose of stem cells is applied, delivered, or administered to the heart or implanted into the heart. An effective dose or amount is an amount sufficient to effect a beneficial or desired clinical result. Said dose could be administered in one or more administrations.

As used herein, "patient" or "subject" may encompass any vertebrate including but not limited to humans, mammals, reptiles, amphibians and fish. However, advantageously, the patient or subject is a mammal such as a human, or a mammal such as a domesticated mammal, e.g., dog, cat, horse, and the like, or production mammal, e.g., cow, sheep, pig, and the like.

It has surprisingly been found that the implantation of somatic stem cells into the myocardium surrounding an infarct following a myocardial infarction, migrate into the damaged area, where they differentiate into myocytes, endothelial cells and smooth muscle cells and then proliferate and form structures including myocardium, coronary arteries, arterioles, and capillaries, restoring the structural and functional integrity of the infarct.

Surprisingly, resident cardiac stem cells (CSCs) have recently been identified in the human (82) and rat (83, 84) heart. These primitive cells tend to accumulate in the atria (82) although they are also present throughout the ventricular myocardium (82, 83, 84). CSCs express surface antigens commonly found in hematopoietic and skeletal muscle stem cells (85, 86). CSCs are clonogenic, self-renewing and multipotent giving rise to all cardiac lineages (84). Because of the growth properties of CSCs, the injured heart has the potential to repair itself. However, this possibility had been limited by our lack of understanding of CSC colonization, proliferation and differentiation in new organized, functioning myocardium (61, 87). Identical obstacles apply to any other source of stem cells in the organism (88).

It is reasonable to suggest that the methods described herein are superior to the procedure employed to replace the necrotic or scarred myocardium by transplanting cardiomyocytes (42, 79), skeletal myoblasts (55, 76) or the prospective utilization of embryonic cells (100, 101). Although these attempts have been successful in the survival of many of the grafted cells, they have failed to reconstitute healthy myocardium and coronary vessels integrated structurally and functionally with the spared portion of the ventricular wall. CSCs are programmed to regulate the normal cell turnover of the heart and, under stressful conditions, participate in the recovery of the injured ventricle structurally and mechanically (82, 102).

The invention provides methods and/or pharmaceutical compositions comprising a therapeutically effective amount of one or more cytokines or cytokine variants for causing the migration and/or proliferation of cardiac stem cells or cardiac primative cells into circulatory tissue or muscle tissue or circulatory muscle tissue, e.g., cardiac tissue, such as the heart or blood vessels—e.g., veins, arteries, that go to or come from the heart such as veins and arteries directly connected or attached or flowing into the heart, for instance the aorta.

Mention is made of U.S. Patent Application Publication No. 2006/0083712 which discloses methods of mobilizing somatic stem cells into the blood stream by administration of cytokines. In contrast to the present invention, the methods disclosed in U.S. Patent Application Publication No. 2006/0083712, which is herein incorporated by reference in its entirety, involve the mobilization of stem cells from the bone marrow into the blood stream where they subsequently home to areas of damage within the heart. In addition, the cytokines used in these methods are distinct from those disclosed in the instant invention.

In a preferred aspect, the methods and/or compositions, including pharmaceutical compositions, comprise effective amounts of two or more cytokines or variants thereof. More specifically, the methods and/or compositions preferably comprise effective amounts of variants of hepatocyte growth factor and optionally insulin-like growth factor-1.

The identification of c-Met on hematopoietic and hepatic stem cells (89, 90, 91) and, most importantly, on satellite skeletal muscle cells (92) has prompted the determining of whether its ligand, hepatocyte growth factor (HGF), has a biological effect on CSCs. HGF positively influences cell migration (93) through the expression and activation of matrix metalloproteinase-2 (94, 95). This enzyme family destroys barriers in the extracellular matrix thereby facilitating CSC movement, homing and tissue restoration. Thus, HGF can mobilize and promote the translocation of CSCs from anatomical storage areas to the site of damage acutely after infarction. Variants of HGF, including substitutions of specific amino acids and splice variants of the full length native transcript (e.g. NK1), exhibit c-MET receptor agonist activity and can mobilize CSCs to sites of tissue damage. Moreover, some of these variants exhibit longer protein half lives and enhanced biological activity compared to full-length HGF.

Insulin-like growth factor-1 (IGF-1) is mitogenic, anti-apoptotic and is necessary for neural stem cell multiplication and differentiation (96, 97, 98). In a comparable manner, IGF-1 impacts CSCs by increasing their number and protecting their viability. IGF-1 overexpression is characterized by myocyte proliferation in the adult mouse heart (65) and this cell growth may depend on CSC activation, differentiation and survival.

Hepatocyte growth factor (HGF) also known as scatter factor (SF) plays a role in the development of epithelial organs, such as the liver, through its activation of the c-MET receptor tyrosine kinase (Schmidt, C. et al, 1995; Bottaro, D. P. et al., 1991). It has also been shown to cause migration of myogenic precursor cells (Bladt et al., 1995) and motor neurons (Caton et al., 2000; Ebens et al., 1996). In addition, HGF has been shown to be effective in mobilizing resident cardiac stem cells to areas of myocardial damage (see U.S. Patent Application Publication No. 2003/0054973, which is herein incorporated by reference in its entirety).

The structure of HGF can be divided into six domains: an N-terminal domain (N), four copies of the kringle domain (K), and a catalytically inactive serine proteinase domain (Donate et al., 1994). The primary HGF transcript can be alternatively spliced to produce two distinct products: NK1 comprised of the N-terminal domain and the first kringle domain, and NK2 containing the N-terminal domain and the first two kringle domains (Cioce et al., 1996; Miyazawa et al., 1991). NK1 has been reported to be a partial agonist of the c-MET receptor (Cioce et al., 1996; Jakubczak et al., 1998).

The natural growth and motility factor HGF acts locally in the tissues in a paracrine manner and, once secreted by producer cells, is sequestered by the extracellular matrix. Heparan sulphate proteoglycans bind HGF with nanomolar affinity. The high pI and the strong affinity of HGF for matrix components are reflected in the behaviour of the recombinant protein in solution. In buffers of low or physiological ionic strength, HGF is polydisperse and aggregated as shown by analytical ultracentrifugation experiments and cannot be eluted from gel filtration columns. However, the protein behaves as a monomer and is stable in buffers containing at least 0.5 M NaCl.

In contrast to full length HGF, the NK1 fragment is considerably more stable in the test tube. The NK1 protein retains the high-affinity binding site for heparan sulphate proteoglycans in the N-terminal domain, but lacks the second, third and fourth kringle domains and the serine proteinase homology domain, resulting in NK1 behaving as stable monomer in solution in buffers of physiological ionic strength. The same applies for engineered derivatives of NK1 such as 1K1 which carries two reverse charge mutations in the kringle 1 domain (K132E and R134E). In addition, variants of HGF with reduced affinity for heparan sulphate proteoglycans were shown to be more stable in the test tube and have a longer half life in vivo (Hartmann et al., 1998).

Variants of NK1 and HGF with altered heparin binding properties were reported to have variable receptor agonist activity (see U.S. Pat. No. 7,179,786, which is herein incorporated by reference in its entirety). NK1 and 1K1 provided enhanced protection compared to HGF against α-amanitin-induced liver failure in mice. In another study, 1K1 and a second mutant of NK1 termed 1K2 (K170E, R181E) showed enhanced biological activity (e.g. stimulation of DNA synthesis, colony scatter activity) compared to wild-type NK1 or full-length HGF (Lietha et al., 2001).

Thus, the present invention provides a method for restoring functional and structural integrity to damaged myocardium in a subject in need thereof by administering an effective amount of at least one variant of hepatocyte growth factor. In one embodiment, the method comprises administering to the subject an effective amount of at least one variant of hepatocyte growth factor to form a chemotactic gradient in the subject's heart sufficient to cause adult cardiac stem cells resident in the heart to replicate and migrate to the area of the damaged myocardium, wherein the functional and structural integrity of the damaged myocardium is restored following the migration of adult cardiac stem cells to the area of damaged myocardium.

The variant of HGF may be selected from the group consisting of NK1, 1K1, 1K2, HP11, and HP21. In one embodiment, the variant of HGF is HP21 (SEQ ID NO: 2). In another embodiment, the variant is HP11 (SEQ ID NO: 3). Preferably the variant of HGF is NK1 (SEQ ID NO: 4) or 1K1 (SEQ ID NO: 5). Other variants of HGF suitable for use in the methods of the invention include HP12 (K58E, K60E, K62E) or 1K2 (K170E, R181E). Amino acid numbers in the mutation designations refer to the position in the wild-type HGF sequence. For example, 1K2 has a glutamate in place of a lysine at position 170 and a glutamate in place of an arginine at position 181, wherein the positions are those in the wild-type HGF sequence (SEQ ID NO: 1).

In some embodiments, the invention includes administering an effective amount of one or more cytokines to a subject's heart (e.g. to an infarcted region or to create a chemotactic gradient). An effective dose is an amount sufficient to effect a beneficial or desired clinical result. Said dose could be administered in one or more administrations. However, the precise determination of what would be considered an effective dose may be based on factors individual to each subject, including their size, age, size of the infarct, the cytokine or combination of cytokines being administered, and amount of time since damage. One skilled in the art, specifically a physician or cardiologist, would be able to determine a sufficient amount of cytokine that would constitute an effective dose without being subjected to undue experimentation. In one embodiment, the at least one variant of hepatocyte growth factor is administered at varying concentrations of about 0.1 to about 400 ng/ml at different places of administration. In another embodiment, the at least one variant of hepatocyte growth factor is administered at varying concentrations of about 50 to about 200 ng/ml at different places of administration. In still another embodiment, the varying concentrations of the at least one variant of hepatocyte growth factor increase progressively in a direction towards the damaged myocardium. In still other embodiments, the at least one variant of hepatocyte growth factor is administered at a concentration of about 10 to about 500 ng/ml, about 20 to about 400 ng/ml, about 30 to about 300 ng/ml, about 50 to about 200 ng/ml, or about 80 to about 150 ng/ml.

In other embodiments, the method further comprises administering a second cytokine in addition to the variant of hepatocyte growth factor to induce proliferation of adult cardiac stem cells. In a preferred embodiment, the second cytokine is insulin-like growth factor-1 (IGF-1). IGF-1 may be administered at a concentration of about 0.1 ng/ml to about 500 ng/ml, about 10 to about 400 ng/ml, about 20 to about 300 ng/ml, about 50 to about 250 ng/ml, about 150 to about 250 ng/ml, or about 200 ng/ml.

A further embodiment of the invention includes the administering of an effective amount of one or more cytokines to the heart by injection. Preferably, the cytokines are delivered to the infarcted region or to the area bordering the infarcted region. As one skilled in the art would be aware, the infarcted area is visible grossly, allowing this specific placement of cytokines to be possible.

The cytokines are advantageously administered by injection, specifically an intramyocardial injection. As one skilled in the art would appreciate, this is the preferred method of delivery for cytokines as the heart is a functioning muscle. Injection of the cytokines into the heart ensures that they will not be lost due to the contracting movements of the heart.

In a further aspect of the invention, the cytokines are administered by injection transendocardially or trans-epicardially. This preferred embodiment allows the cytokines to penetrate the protective surrounding membrane, necessitated by the embodiment in which the cytokines are injected intramyocardially. A preferred embodiment of the invention includes use of a catheter-based approach to deliver the transendocardial injection. The use of a catheter precludes more invasive methods of delivery wherein the opening of the chest cavity would be necessitated.

In a further embodiment of the invention, cytokines are delivered to the subject's heart by a single administration. In another embodiment, cytokines are delivered to the subject's heart by multiple administrations of the same dosage of cytokines. In yet another embodiment, the invention includes administration of multiple doses of the cytokines to the heart, such that a chemotactic gradient is formed. For example, in one embodiment, a method for restoring functional and structural integrity to damaged myocardium in a subject in need thereof comprises administering to the subject an effective amount of at least one variant of hepatocyte growth factor to form a chemotactic gradient in the subject's heart sufficient to cause adult cardiac stem cells resident in the heart to replicate and migrate to the area of the damaged myocardium, wherein said gradient is formed by multiple injections of said at least one variant of hepatocyte growth factor from storage areas of said resident adult cardiac stem cells to a border zone of the damaged myocardium, and wherein the functional and structural integrity of the damaged myocardium is restored following the migration of adult cardiac stem cells to the area of damaged myocardium. Storage areas of resident adult cardiac stem cells may include one or more of the subject's myocardial apex, left atrium, and right atrium. In one embodiment, the multiple injections comprise variable concentrations of said variant of hepatocyte growth factor. In another embodiment, at least two of the injections are done at opposite sides of the border zone.

The present invention also provides methods and/or pharmaceutical compositions comprising a therapeutically effective amount of somatic stem cells alone or in combination with one or more cytokines described above. Thus, the invention involves the use of somatic stem cells. These are present in animals in small amounts, but methods of collecting stem cells are known to those skilled in the art.

In one aspect of the invention, the stem cells are selected to be lineage negative. The term "lineage negative" is known to one skilled in the art as meaning the cell does not express antigens characteristic of specific cell lineages. Advantageously, the lineage negative stem cells are selected to be c-kit positive. The term "c-kit" is known to one skilled in the art as being a receptor which is known to be present on the surface of stem cells, and which is routinely utilized in the process of identifying and separating stem cells from other surrounding cells.

The invention further involves a therapeutically effective dose or amount of stem cells applied to the heart. An effective dose is an amount sufficient to effect a beneficial or desired clinical result. Said dose could be administered in one or more administrations. Effective doses could be determined by the skilled artisan as described in U.S. Patent Application Publication No. 2006/0239983, which is herein incorporated by reference in its entirety. U.S. Patent Application Publication No. 2006/0239983 discloses methods of activating and using isolated adult stem cells for regenerating damaged myocardium and coronary vasculature, and describes examples in which $2 \times 10^4$-$1 \times 10^5$ stem cells were administered in a mouse model of myocardial infarction. While there would be an obvious size difference between the hearts of a mouse and a human, it is possible that this range of stem cells would be sufficient in a human as well. However, the precise determination of what would be considered an effective dose may be based on factors individual to each patient, including their size, age, size of the infarct, and amount of time since damage. One skilled in the art, specifically a physician or cardiologist, would be able to determine the number of stem cells that would constitute an effective dose without undue experimentation from this disclosure and the knowledge in the art; and, in this regard and in general in regard to preparing formulations and administering formulations or components thereof. The stem cells are advantageously bone marrow or are cardiac stem cells; and even more advantageously, the stem cells are adult bone marrow (hematopoietic stem cells) or adult cardiac stem cells or a combination thereof or a combination of cardiac stem cells such as adult cardiac stem cells and another type of stem cell such as another type of adult stem cells.

In another aspect of the invention, the stem cells are delivered to the heart, specifically to the border area of the infarct. As one skilled in the art would be aware, the infarcted area is visible grossly, allowing this specific placement of stem cells to be possible.

The stem cells are advantageously administered by injection, specifically an intramyocardial injection. Injection of the stem cells into the heart ensures that they will not be lost due to the contracting movements of the heart. In another embodiment, the cardiac stem cells are administered intracoronarily.

In a further aspect of the invention, the stem cells are administered by injection transendocardially or trans-epicardially. This preferred embodiment allows the stem cells to penetrate the protective surrounding membrane, necessitated by the embodiment in which the cells are injected intramyocardially.

A preferred embodiment of the invention includes use of a catheter-based approach to deliver the trans-endocardial injection. The use of a catheter precludes more invasive methods of delivery wherein the opening of the chest cavity would be necessitated. As one skilled in the art is aware, optimum time of recovery would be allowed by the more minimally invasive procedure, which as outlined here, includes a catheter approach.

A catheter approach includes the use of such techniques as the NOGA catheter or similar systems. The NOGA catheter system facilitates guided administration by providing electromechanic mapping of the area of interest, as well as a retractable needle that can be used to deliver targeted injections or to bathe a targeted area with a therapeutic. Any of the embodiments of the present invention can be administered through the use of such a system to deliver injections or provide a therapeutic. One of skill in the art will recognize alternate systems that also provide the ability to provide targeted treatment through the integration of imaging and a catheter delivery system that can be used with the present invention. Information regarding the use of NOGA and similar systems can be found in, for example, Sherman, 2003; Patel, 2005; and Perrin, 2003; the text of each of which are incorporated herein in their entirety.

Further embodiments of the invention require the stem cells to migrate into the infarcted region and differentiate into myocytes, smooth muscle cells, and endothelial cells. Another embodiment of the invention includes the proliferation of the differentiated cells and the formation of the cells into cardiac structures including coronary arteries, arterioles, capillaries, and myocardium (e.g. myocardial tissue and myocardial vessels). It is known in the art that these types of cells and structures must be present to restore both structural and functional integrity. Other approaches to repairing infarcted or ischemic tissue have involved the implantation of these differentiated cells directly into the heart, or as cultured grafts, such as in U.S. Pat. Nos. 6,110,459, and 6,099,832. It has been shown in the literature that implantation of cells including endothelial cells and smooth muscle cells will allow for the implanted cells to live within the infarcted region, however they do not form the necessary structures to enable the heart to regain full functionality. The ability to restore both functional and structural integrity is yet another aspect of this invention.

A still further embodiment of the invention includes the stimulation, migration, proliferation and/or differentiation of the resident cardiac stem cells.

It is a preferred in the practice of the invention to utilize both the administration of stem cells and that of a cytokine to ensure the most effective method of repairing damaged myocardium.

The invention also encompasses methods and compositions for the treatment of vasculature disorders or disease, including the occlusion or blockage of a coronary artery or vessel. These methods and compositions can be used for such therapeutic treatment as an alternative to, or in combination with, cardiac bypass surgery. Thus, the present invention provides for the isolation, expansion, activation, and implantation or delivery of activated stem cells, preferably activated cardiac stem cells, to an area of the vasculature in need thereof. Such delivery or implantation can be accomplished by any of the methods described herein or which are known to those of skill in the art, including, but not limited to, the use of a NOGA catheter system such that visualization of the area to be treated is possible, and the therapeutic is delivered via a retractable needle associated with such catheter system. One of skill in the art will recognize other useful methods of delivery or implantation which can be utilized with the present invention, including those described in Dawn, 2005, the contents of which are incorporated herein in their entirety.

In one embodiment, cardiac tissue is harvested from a patient in need of therapeutic treatment for one of the cardiac or vasculature conditions described herein. The present invention provides for the isolation of stem cells, preferably cardiac stem cells, more preferably c-kit$^{POS}$ cardiac stem cells, which are cultured and expanded in vitro.

In another embodiment, the present invention provides media for use in the culture and expansion of stem cells, preferably cardiac stem cells, more preferably human c-kit$^{POS}$ cardiac stem cells. Such media can comprise DMEM/F12, patient serum, insulin, transferrin and sodium selenite. In one embodiment, the media can further comprise one or more of human recombinant bFGF, human recombinant EGF, uridine and inosine.

In another embodiment, components of the medium can be present in approximate ranges as follows:

| Component | Final Concentration |
|---|---|
| Patient serum | 5-20% by weight |
| Human recombinant bFGF | 10-100 ng/mL |
| Human recombinant EGF | 10-100 ng/mL |
| Insulin | 2-20 µg/mL |
| Transferrin | 2-20 µg/mL |
| Sodium selenite | 2-10 ng/mL |
| Uridine | 0.24-2.44 mg/mL |
| Inosine | 0.27-2.68 mg/mL |

In another embodiment, substitutions of the components of the media may be made as known by those of skill in the art. For example, insulin can be substituted with insulin-like growth factor-1. Uridine and inosine can be substituted with mixtures of other nucleotides, including adenosine, guanosine, xanthine, thymidine, and cytidine.

In one embodiment of the present invention, the above media can be utilized during the culturing and expansion of stem cells that are to be administered in order to regenerate or create new myocardium in a damaged or infacted area of the heart.

In another embodiment of the invention, the cultured and expanded stem cells, preferably cardiac stem cells, more preferably human c-kit$^{POS}$ cardiac stem cells, are activated prior to their implantation or delivery. Thus, the present invention provides a method of activating adult cardiac stem cells comprising incubating isolated adult cardiac stem cells in a solution comprising at least one cytokine. Cytokines or growth factors suitable for use in the method of the invention include any of those described herein, including, but not limited to: Activin A, Angiotensin II, Bone Morphogenic Protein 2, Bone Morphogenic Protein 4, Bone Morphogenic Protein 6, Cardiotrophin-1, Fibroblast Growth Factor 1, Fibroblast Growth Factor 4, Flt3 Ligand, Glial-Derived Neurotrophic Factor, Heparin, Hepatocyte Growth Factor, Insulin-like Growth Factor-1, Insulin-like Growth Factor-II, Insulin-Like Growth Factor Binding Protein-3, Insulin-Like Growth Factor Binding Protein-5, Interleukin-3, Interleukin-6, Interleukin-8, Leukemia Inhibitory Factor, Midkine, Platelet-Derived Growth Factor AA, Platelet-Derived Growth Factor BB, Progesterone, Putrescine, Stem Cell Factor, Stromal-Derived Factor-1, Thrombopoietin, Transforming Growth Factor-α, Transforming Growth Factor-β1, Transforming Growth Factor-.β2, Transforming Growth Factor-β3, Vascular Endothelial Growth Factor, Wnt1, Wnt3a, and Wnt5a, as described in Ko, 2006; Kanemura, 2005; Kaplan, 2005; Xu, 2005; Quinn, 2005; Almeida, 2005; Barnabe-Heider, 2005; Madlambayan, 2005; Kamanga-Sollo, 2005; Heese, 2005; He, 2005; Beattie, 2005; Sekiya, 2005; Weidt, 2004; Encabo, 2004; and Buytaeri-Hoefen, 2004, the entire text of each of which is incorporated herein by reference. One of skill in the art will be able to select one or more appropriate cytokines or growth factors. In one embodiment, the stem cells are contacted with hepatocyte growth factor (HGF) and/or insulin-like growth factor-1 (IGF-1). In a preferred embodiment, the stem cells are activated by incubating the stem cells with a solution comprising a variant of HGF as described herein. The variant of HGF may include NK1, 1K1, 1K2, HP11, or HP21. In one embodiment, the variant of HGF is NK1. In another embodiment, the variant of HGF is 1K1. In another embodiment, the HGF or variant of HGF is present in an amount of about 0.1 to about 400 ng/ml. In a further embodiment, the HGF or variant thereof is present in an amount of about 25, about 50, about 75, about 100, about 125, about 150, about 175, about 200, about 225, about 250, about 275, about 300, about 325, about 350, about 375 or about 400 ng/ml.

In another embodiment, the activation solution further comprises a second cytokine, wherein the second cytokine induces proliferation of adult cardiac stem cells. In another embodiment, the second cytokine is IGF-1. The IGF-1 may be present in an amount of about 0.1 to about 500 ng/ml. In yet a further embodiment, the IGF-1 is present in an amount of about 25, about 50, about 75, about 100, about 125, about 150, about 175, about 200, about 225, about 250, about 275, about 300, about 325, about 350, about 375, about 400, about 425, about 450, about 475, or about 500 ng/ml.

In yet a still further embodiment, the one or more cytokines or growth factors can be present in the media provided herein, such that in one embodiment, the media comprises one or more growth factors or cytokines, DMEM/F12, patient serum, insulin, transferrin and sodium selenite and optionally one or more of human recombinant bFGF, human recombinant EGF, uridine and inosine. It is contemplated that the components of the media can be present in the amounts described herein, and one of skill in the art will be able to determine a sufficient amount of the one or more growth factors or cytokines in order to obtain activation of any stem cells contacted therewith.

In one embodiment of the present invention, activated stem cells, preferably activated cardiac stem cells, more preferable activated human c-kit$^{POS}$ cardiac stem cells are delivered to, or implanted in, an area of the vasculature in need of therapy or repair. For example, in one embodiment the activated stem cells are delivered to, or implanted in, the site of an occluded or blocked cardiac vessel or artery. In one embodiment of the present invention, cardiac stem cells that are c-kit$^{POS}$ are delivered to, or implanted in, the area in need of therapy or repair. In another embodiment of the invention, the activated stem cells form into an artery or vessel at the site at which the stem cells were delivered or implanted. In one embodiment, the formed artery or vessel has a diameter ranging from about 6 to about 250 µm, wherein the artery or vessel is formed within one month after administration of the activated cardiac stem cells. In yet a further embodiment, the formed artery or vessel has a diameter of over 100 µm. In yet a further embodiment, the formed artery or vessel has a diameter of at least 125, at least 150, at least 175, at least 200, at least 225, at least 250 or at least 275 µm. In yet another embodiment of the present invention, the formed artery or vessel provides a "biological bypass" around the area in need of therapy or repair, including around an occlusion or blockage such that blood flow, blood pressure, and circulation are restored or improved. In yet a still further embodiment of the present invention, the administration of activated stem cells can be done in conjunction with other therapeutic means, including but not limited to the administration of other therapeutics, including one or more growth factors or cytokines.

In another embodiment, the present invention provides a method for restoring structural and functional integrity to damaged myocardium in a subject in need thereof comprising extracting cardiac stem cells from the subject; culturing and expanding said cardiac stem cells; activating the extracted and expanded cardiac stem cells by exposing the cardiac stem cells to at least one cytokine; and administering an effective dose of said activated cardiac stem cells to an area of damaged myocardium in the subject, wherein the activated cardiac stem cells restore structural and functional integrity to the damaged myocardium following their administration. In one embodiment, the at least one cytokine is a variant of hepatocyte growth factor.

One embodiment of the invention includes the proliferation of the differentiated cells and the formation of the cells into cardiac structures including coronary arteries, arterioles, capillaries, and myocardium. As one skilled in the art is aware, all of these structures are essential for proper function in the heart. It has been shown in the literature that implantation of cells including endothelial cells and smooth muscle cells will allow for the implanted cells to live within the infarcted region, however they do not form the necessary structures to enable the heart to regain full functionality. Cardiac structures can be generated ex vivo and then implanted in the form of a graft; with the implantation of the graft being alone or in combination with stem cells or stem cells and at least one cytokine as in this disclosure, e.g., advantageously adult or cardiac or hematopoietic stem cells such as adult cardiac and/or adult hematpoietic stem cells or adult cardiac stem cells with another type of stem cell e.g. another type of adult stem cell. The means of generating and/or regenerating myocardium ex vivo, may incorporate somatic stem cells and heart tissue being cultured in vitro, optionally in the presence of a cytokine. The somatic stem cells differentiate into myocytes, smooth muscle cells and endothelial cells, and proliferate in vitro, forming myocardial tissue and/or cells. These tissues and cells may assemble into cardiac structures including arteries, arterioles, capillaries, and myocardium. The tissue and/or cells formed in vitro may then be implanted into a patient, e.g. via a graft, to restore structural and functional integrity.

Additionally or alternatively, the source of the tissue being grafted can be from other sources of tissue used in grafts of the heart.

The restoration or some restoration of both functional and structural integrity of cardiac tissue—advantageously over that which has occurred previously—is yet another aspect of this invention.

The invention comprehends, in further aspects, methods for preparing compositions such as pharmaceutical compositions including somatic stem cells and/or at least one cytokine, for instance, for use in inventive methods for treating cardiovascular disease or conditions or cardiac conditions.

The cytokines in the pharmaceutical composition of the present invention may also include mediators known to be involved in the maintenance of early and late hematopoiesis such as IL-1 alpha and IL-1 beta, IL-6, IL-7, IL-8, IL-11 and IL-13; colony-stimulating factors, thrombopoietin, erythropoietin, stem cell factor, fit 3-ligand, hepatocyte cell growth factor or variants thereof, tumor necrosis factor alpha, leukemia inhibitory factor, transforming growth factors beta 1 and beta 3; and macrophage inflammatory protein 1 alpha), angiogenic factors (fibroblast growth factors 1 and 2, vascular endothelial growth factor) and mediators whose usual target (and source) is the connective tissue-forming cells (platelet-derived growth factor A, epidermal growth factor, transforming growth factors alpha and beta 2, oncostatin M and insulin-like growth factor-1), or neuronal cells (nerve growth factor) (Sensebe, L., et al., Stem Cells 1997; 15:133-43), VEGF polypeptides that are present in platelets and megacaryocytes (Wartiovaara, U., et al., *Thromb Haemost* 1998; 80:171-5; Mohle, R., *Proc Natl Acad Sci USA* 1997; 94:663-8) HIF-1, a potent transcription factor that binds to and stimulates the promoter of several genes involved in responses to hypoxia, endothelial PAS domain protein 1 (EPAS 1), monocyte-derived cytokines for enhancing collateral function such as monocyte chemotactic protein-1 (MCP-1).

In an additionally preferred aspect, the methods and/or compositions, including pharmaceutical compositions, comprise effective amounts of two or more cytokines or variants thereof in combination with an appropriate pharmaceutical agent useful in treating cardiac and/or vascular conditions.

In a preferred aspect, the pharmaceutical composition of the present invention is delivered via injection. These routes for administration (delivery) include, but are not limited to subcutaneous or parenteral including intravenous, intraarterial, intramuscular, intraperitoneal, intramyocardial, intracoronarial, transendocardial, trans-epicardial, intranasal administration as well as intrathecal, and infusion techniques. Hence, preferably the pharmaceutical composition is in a form that is suitable for injection.

When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various amounts of the other ingredients, as desired.

The pharmaceutical composition of the present invention, e.g., comprising a therapeutic compound, can be administered to the patient in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as monoclonal antibodies, iontophoretic, polymer matrices, liposomes, and microspheres.

The pharmaceutical composition utilized in the present invention can be administered orally to the patient. Conventional methods such as administering the compounds in tablets, suspensions, solutions, emulsions, capsules, powders, syrups and the like are usable. Known techniques which deliver the compound orally or intravenously and retain the biological activity are preferred.

In one embodiment, a composition of the present invention can be administered initially, and thereafter maintained by further administration. For instance, a composition of the invention can be administered in one type of composition and thereafter further administered in a different or the same type of composition. For example, a composition of the invention can be administered by intravenous injection to bring blood levels to a suitable level. The patient's levels are then maintained by an oral dosage form, although other forms of administration, dependent upon the patient's condition, can be used.

It is noted that humans are treated generally longer than the mice or other experimental animals which treatment has a length proportional to the length of the disease process and drug effectiveness. The doses may be single doses or multiple doses over a period of several days, but single doses are preferred. Thus, one can scale up from animal experiments, e.g., rats, mice, and the like, to humans, by techniques from this disclosure and documents cited herein and the knowledge in the art, without undue experimentation.

The treatment generally has a length proportional to the length of the disease process and drug effectiveness and the patient being treated.

The quantity of the pharmaceutical composition to be administered will vary for the patient being treated. In a preferred embodiment, $2 \times 10^4 - 1 \times 10^5$ stem cells and 50-500 µg/kg per day of a cytokine or variant of said cytokine are administered to the patient. While there would be an obvious size difference between the hearts of a mouse and a human, it is possible that $2 \times 10^4 - 1 \times 10^5$ stem cells would be sufficient in a human as well. However, the precise determination of what would be considered an effective dose may be based on factors individual to each patient, including their size, age, size of the infarct, and amount of time since damage. Therefore, dosages can be readily ascertained by those skilled in the art from this disclosure and the knowledge in the art. Thus, the skilled artisan can readily determine the amount of compound and optional additives, vehicles, and/or carrier in compositions and to be administered in methods of the invention. Typically, any additives (in addition to the active stem cell(s) and/or cytokine(s)) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Additionally, one of skill in the art would be able to ascertain without undue experimentation the appropriate pharmaceutical agent to be used in combination with one or more cytokines; and, one of skill in the art would be able to make the precise determination of what would be considered an effective dose based on factors individual to each patient, including their size, age, size of the infarct, and amount of time since damage. Therefore, dosages can be readily ascertained by those skilled in the art from this disclosure and the knowledge in the art.

Examples of compositions comprising a therapeutic of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention can be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally. The viscous compositions may be in the form of gels, lotions, ointments, creams and the like (e.g., for transdermal administration) and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally. Viscous compositions, on the other hand, can be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels normally contain a major amount of water (preferably purified water) in addition to the active compound. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems can be readily avoided by reference to standard texts or by simple experiments (not involving undue experimentation), from this disclosure and the documents cited herein.

The inventive compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

The pharmaceutical compositions of the present invention are used to treat cardiovascular diseases, including, but not limited to, atherosclerosis, ischemia, hypertension, restenosis, angina pectoris, rheumatic heart disease, congenital cardiovascular defects and arterial inflammation and other diseases of the arteries, arterioles and capillaries or related complaint. Accordingly, the invention involves the administration of stem cells as herein discussed, alone or in combination with one or more cytokine or variant of said cytokine, as herein discussed, for the treatment or prevention of any one or more of these conditions or other conditions involving weakness in the heart, as well as compositions for such treatment or prevention, use of stem cells as herein discussed, alone or in combination with one or more cytokine or variant thereof, as herein discussed, for formulating such compositions, and kits involving stem cells as herein discussed, alone or in combination with one or more cytokine or cytokine variant, as herein discussed, for preparing such compositions and/or for such treatment, or prevention. And, advantageous routes of administration involves those best suited for treating these conditions, such as via injection, including, but are not limited to subcutaneous or parenteral including intravenous, intraarterial, intramuscular, intraperitoneal, intramyocardial, intracoronarial, transendocardial, trans-epicardial, intranasal administration as well as intrathecal, and infusion techniques.

The present invention is additionally described by way of the following, non-limiting examples, that provide a better understanding of the present invention and its many advantages.

EXAMPLES

Example 1

Variants of HGF Induce Proliferation of Human Cardiac Stem Cells

Myocardial tissue (averaging 1 g or less in weight) was harvested from consenting patients who underwent cardiac surgery under sterile conditions in the operating room. Samples were minced and seeded onto the surface of uncoated Petri dishes containing a medium supplemented with hepatocyte growth factor and insulin-like growth factor-1 at concentrations of 200 ng/ml. Cells outgrown from the tissue were sorted for c-kit with immunobeads and cultured (Beltrami, 2003; Linke, 2005). Cell phenotype was defined by FACS and immunocytochemistry as described previously (Beltrami, 2003; Orlic, 2001; Urbanek, 2005).

The human c-kit positive cells (human cardiac stem cells, hCSCs) were plated in 35 mm diameter culture dishes at the same density and cultured under standard conditions in F12 medium with 10% fetal bovine serum (FBS) for at least 48 hours to support cell attachment and settling. At 70-80% confluence, medium was changed and a two-step starvation was performed, reducing the initial FBS concentration to 5% and, after 24 hours to 0.5%. After 24 hours in 0.5% FBS, hepatocyte growth factor (HGF) or a variant of HGF (HP21, HP11, NK1, or 1K1) were added at a molar concentration equivalent to 100 ng/ml of HGF, i.e., $1,245 \times 10^{-15}$ M to each culture dish and kept in an incubator, under sterile conditions (37° C., 5% $CO_2$ atmosphere). Nothing was added to control cultures. BrdU (1 µg/ml) was added three times every twelve hours. After 24 hours of incubation, culture dishes were fixed in ethanol fixative and proliferation was detected and measured via BrdU labeling (Roche Applied Science). The percentage of BrdU labeled cells for each condition is shown in Table 1 below.

TABLE 1

Proliferation of human cardiac stem cells induced by variants of HGF.

|  | experiment | BrdU(+) cells | total cells | % BrdU(+) cells | Fold increase over control |
|---|---|---|---|---|---|
| HGF/SF (SEQ ID NO: 1) | 1 | 101 | 942 | 10.72 | |
| | 2 | 121 | 1290 | 9.38 | |
| | 3 | 72 | 860 | 8.37 | |
| | 4 | 107 | 622 | 17.20 | |
| | 5 | 123 | 777 | 15.83 | |
| | 6 | 77 | 888 | 8.67 | |
| | 7 | 100 | 1217 | 8.22 | |
| | | | average | 11.2 | 2.2-fold |
| | | | SD | 3.7 | |
| HP21 (R73E) (SEQ ID NO: 2) | 1 | 125 | 1062 | 11.77 | |
| | 2 | 73 | 630 | 11.59 | |
| | 3 | 101 | 1014 | 9.96 | |
| | 4 | 75 | 919 | 8.16 | |
| | 5 | 63 | 935 | 6.74 | |
| | 6 | 36 | 604 | 5.96 | |
| | 7 | 77 | 587 | 13.12 | |
| | | | average | 9.6 | 1.9-fold |
| | | | SD | 2.7 | |
| HP11 (R73E, R76E) (SEQ ID NO: 3) | 1 | 132 | 1012 | 13.04 | |
| | 2 | 88 | 485 | 18.14 | |
| | 3 | 125 | 913 | 13.69 | |
| | 4 | 108 | 376 | 28.72 | |
| | 5 | 72 | 743 | 9.69 | |
| | 6 | 52 | 604 | 8.61 | |
| | 7 | 48 | 586 | 8.19 | |
| | | | average | 14.3 | 2.8-fold |
| | | | SD | 6.7 | |
| NK1 (SEQ ID NO: 4) | 1 | 121 | 1254 | 9.65 | |
| | 2 | 80 | 567 | 14.11 | |
| | 3 | 101 | 461 | 21.91 | |
| | 4 | 107 | 596 | 17.95 | |
| | 5 | 116 | 1556 | 7.46 | |
| | 6 | 36 | 382 | 9.42 | |
| | 7 | 38 | 609 | 6.24 | |
| | | | average | 12.4 | 2.4-fold |
| | | | SD | 5.4 | |
| 1K1 (K132E, R134E) (SEQ ID NO: 5) | 1 | 122 | 1155 | 10.56 | |
| | 2 | 70 | 871 | 8.04 | |
| | 3 | 108 | 507 | 21.30 | |
| | 4 | 101 | 904 | 11.17 | |
| | 5 | 103 | 1201 | 8.58 | |
| | 6 | 60 | 686 | 8.75 | |
| | 7 | 60 | 617 | 9.72 | |
| | | | average | 11.2 | 2.2-fold |
| | | | SD | 4.6 | |
| ctrl | 1 | 54 | 888 | 6.08 | |
| | 2 | 103 | 1258 | 8.19 | |
| | 3 | 53 | 1022 | 5.19 | |
| | 4 | 62 | 1120 | 5.54 | |
| | 5 | 37 | 1208 | 3.06 | |
| | 6 | 14 | 505 | 2.77 | |
| | | | average | 5.1 | |
| | | | SD | 2.0 | |

The amino acid numbers in the mutation designations refer to the amino acid positions in the wild-type HGF protein (SEQ ID NO: 1). Note that the HGF used in this Example and the following examples did not contain the first 31 amino acids (leader sequence) of SEQ ID NO: 1 as these amino acids are cleaved upon secretion of the peptide from the cells, so that the active molecule does not posses this leader sequence. NK1 is a natural splice variant of HGF and contains amino acids 32-206 of the wild-type HGF protein. SEQ ID NO: 4 includes an additional four amino acids at the N- and C-terminus for experimental convenience. 1K1 is a mutant of NK1 and contains amino acid substitutions as designated at positions 132 and 134. The results of this experiment show that all of the HGF variants could induce proliferation of hCSCs approximately 2 fold over controls. The HP11 variant appeared to induce the greatest amount of proliferation.

Example 2

Variants of HGF Reduce Apoptosis of Human Cardiac Stem Cells In Vitro

Human cardiac stem cells (c-kit positive cells) were plated in 35 mm diameter culture dishes at the same density and cultured under standard conditions in F12 medium with 10% FBS for at least 48 hours to support cell attachment and settling. At 70-80% confluence, medium was changed and HGF or a variant of HGF (HP21, HP11, NK1, or 1K1) was added at a molar concentration of 100 ng/ml, corresponding to $1,245 \times 10^{-15}$ M to each culture dish and kept in an incubator, under sterile conditions (37° C., 5% $CO_2$ atmosphere). Nothing was added to control cultures. One hour after growth factor addition, xanthine (0.5 mM) and xanthine oxidase (100 mU/ml) were applied to each culture, including control cultures, to induce apoptosis. 24 hours after addition of the apoptotic stimuli, culture dishes were fixed in 4% methanol-free formaldehyde in HBSS for 20 minutes in ice and stored for one hour in 70% ethanol at −20° C. Apoptosis was detected and measured via TdT labelling (Apoalert DNA Fragmentation Kit, Clontech). The results of the apoptosis assay are depicted in Table 2.

TABLE 2

Variants of HGF reduce apoptosis in hCSCs in vitro.

|  | experiment | Tunel(+) cells | total cells | % apoptotic cells | % decrease compared to control |
|---|---|---|---|---|---|
| HGF/SF (SEQ ID NO: 1) | 1 | 12 | 234 | 5.13 |  |
|  | 2 | 14 | 275 | 5.09 |  |
|  | 3 | 13 | 251 | 5.18 |  |
|  | 4 | 11 | 237 | 4.64 |  |
|  | 5 | 6 | 172 | 3.49 |  |
|  | 6 | 11 | 199 | 5.53 |  |
|  | 7 | 17 | 123 | 13.82 |  |
|  | 8 | 14 | 101 | 13.86 |  |
|  | 9 | 8 | 126 | 6.35 |  |
|  | average |  |  | 7.0 | −78.6% decrease |
|  | SD |  |  | 3.9 |  |
| HP21 (R73E) (SEQ ID NO: 2) | 5 | 5 | 91 | 5.49 |  |
|  | 6 | 7 | 101 | 6.93 |  |
|  | 7 | 13 | 176 | 7.39 |  |
|  | 8 | 10 | 95 | 10.53 |  |
|  | 9 | 15 | 136 | 11.03 |  |
|  | average |  |  | 8.3 | −74.7% decrease |
|  | SD |  |  | 2.4 |  |
| HP11 (R73E, R76E) (SEQ ID NO: 3) | 1 | 10 | 301 | 3.32 |  |
|  | 2 | 19 | 607 | 3.13 |  |
|  | 3 | 10 | 103 | 9.71 |  |
|  | 4 | 9 | 145 | 6.21 |  |
|  | 5 | 19 | 142 | 13.38 |  |
|  | 6 | 15 | 156 | 9.62 |  |
|  | 7 | 63 | 717 | 8.79 |  |
|  | 8 | 31 | 243 | 12.76 |  |
|  | 9 | 20 | 187 | 10.70 |  |
|  | average |  |  | 8.6 | −73.6% decrease |
|  | SD |  |  | 3.7 |  |
| NK1 (SEQ ID NO: 4) | 5 | 16 | 60 | 26.67 |  |
|  | 6 | 14 | 53 | 26.42 |  |
|  | 7 | 18 | 74 | 24.32 |  |
|  | 8 | 15 | 41 | 36.59 |  |
|  | 9 | 21 | 52 | 40.38 |  |
|  | average |  |  | 30.9 | −5.6% decrease |
|  | SD |  |  | 6.4 |  |
| 1K1 (K132E, R134E) (SEQ ID NO: 5) | 5 | 17 | 47 | 36.17 |  |
|  | 6 | 11 | 46 | 23.91 |  |
|  | 7 | 12 | 52 | 23.08 |  |
|  | 8 | 18 | 38 | 47.37 |  |
|  | 9 | 14 | 53 | 26.42 |  |
|  | average |  |  | 31.4 | −4.0% decrease |
|  | SD |  |  | 9.3 |  |
| ctrl | 1 | 23 | 115 | 20.00 |  |
|  | 3 | 31 | 145 | 21.38 |  |

TABLE 2-continued

Variants of HGF reduce apoptosis in hCSCs in vitro.

| experiment | Tunel(+) cells | total cells | % apoptotic cells | % decrease compared to control |
|---|---|---|---|---|
| 5 | 25 | 127 | 19.69 | |
| 7 | 27 | 67 | 40.30 | |
| 8 | 28 | 74 | 37.84 | |
| 9 | 32 | 56 | 57.14 | |
| | | average | 32.7 | 0.1% decrease |
| | | SD | 13.8 | |

These results show that variants of HGF, in particular the full-length variants (HP21 and HP11) drastically reduce the number of hCSCs that undergo apoptosis in response to an inducing stimulus.

Example 3
NK1 and Other HGF Variants Mobilize Human Cardiac Stem Cells to Sites of Injury The purpose of this experiment was to examine the ability of NK1 and other HGF variants to induce migration of hCSCs to injured tissue in an in vitro wound healing assay. This in vitro methodology consists of the disruption of the confluent layer of cells in the culture dish. Subsequently, the ability of the tested cells to migrate towards the disrupted area is measured in terms of number of cells and speed of locomotion. Both the speed of stem cell migration towards the wound and the number of stem cells found in the wound area were calculated. The results are shown in Tables 3 and 4.

TABLE 3

Migration rate of stem cells towards a wound in vitro.

| | | Ctrl | HGF/SF | HGF/SF R73E (HP21) | HGF/SF R73E:R76E (HP11) | NK1 (NK1) | NK1 K132E:K134E (1K1) |
|---|---|---|---|---|---|---|---|
| Migration (μm/hr) | | | | | | | |
| May 23, 2007 set #1 | DHT 0083 p5 | 6.5 | 7.6 | 13.6 | 9.1 | 10.1 | 3.6 |
| May 23, 2007 set #2 | DHT 0083 p5 | 4.6 | 11.8 | 7.9 | 10.5 | 8.2 | 8.7 |
| May 25, 2007 set #1 | DHT 0083 p7 | 8.9 | 15.4 | 16.1 | 12.5 | 11.6 | 16.3 |
| May 25, 2007 set #2 | DHT 0083 p7 | 12.3 | 17.8 | 20.9 | 11.9 | 17.9 | 13.5 |
| May 25, 2007 set #3 | DHT 0083 p7 | 12.5 | 20.5 | 21.9 | 15.2 | 20.5 | 17.9 |
| May 25, 2007 set #4 | DHT 0083 p7 | 10.7 | 16.7 | 17.1 | 20.3 | 17.7 | 17.5 |
| Jun. 18, 2007 set #1 | DHT 0098 p2 | 10.9 | 16.5 | 14.7 | 15.5 | 15.9 | 14.5 |
| Jun. 18, 2007 set #2 | DHT 0098 p2 | 11.3 | 19.8 | 18.4 | 14.6 | 16.4 | 17.1 |
| Jun. 18, 2007 set #3 | DHT 0098 p2 | 10.7 | 17.2 | 17.5 | 18.2 | 17.3 | 16.1 |
| Jun. 27, 2007 set #1 | DHT 0098 p5 | 7.1 | 11.3 | 15.4 | 9.4 | 10.7 | 10.7 |
| Jun. 27, 2007 set #2 | DHT 0098 p5 | 6.5 | 11.9 | 13.0 | 12.1 | 11.4 | 9.2 |
| average | | 9.3 | 15.1 | 16.0 | 13.6 | 14.3 | 13.2 |
| standard deviation | | 2.7 | 4.0 | 3.9 | 3.6 | 4.0 | 4.6 |
| Fold increase in migration rate | | | | | | | |
| May 23, 2007 set #1 | DHT 0083 p5 | 1 | 1.2 | 2.1 | 1.4 | 1.6 | 0.6 |
| May 23, 2007 set #2 | DHT 0083 p5 | 1 | 2.6 | 1.7 | 2.3 | 1.8 | 1.9 |
| May 25, 2007 set #1 | DHT 0083 p7 | 1 | 1.7 | 1.8 | 1.4 | 1.3 | 1.8 |
| May 25, 2007 set #2 | DHT 0083 p7 | 1 | 1.4 | 1.7 | 1.0 | 1.5 | 1.1 |
| May 25, 2007 set #3 | DHT 0083 p7 | 1 | 1.6 | 1.8 | 1.2 | 1.6 | 1.4 |
| May 25, 2007 set #4 | DHT 0083 p7 | 1 | 1.6 | 1.6 | 1.9 | 1.7 | 1.6 |
| Jun. 18, 2007 set #1 | DHT 0098 p2 | 1 | 1.5 | 1.3 | 1.4 | 1.5 | 1.3 |
| Jun. 18, 2007 set #2 | DHT 0098 p2 | 1 | 1.8 | 1.6 | 1.3 | 1.5 | 1.5 |
| Jun. 18, 2007 set #3 | DHT 0098 p2 | 1 | 1.6 | 1.6 | 1.7 | 1.6 | 1.5 |
| Jun. 27, 2007 set #1 | DHT 0098 p5 | 1 | 1.6 | 2.2 | 1.3 | 1.5 | 1.5 |
| Jun. 27, 2007 set #2 | DHT 0098 p5 | 1 | 1.8 | 2.0 | 1.9 | 1.8 | 1.4 |
| average | | 1 | 1.7 | 1.8 | 1.5 | 1.6 | 1.4 |
| standard deviation | | 0 | 0.3 | 0.2 | 0.4 | 0.1 | 0.4 |

TABLE 4

Number of stem cells found in the wound area due to migration.

| | | ctrl | HGF/SF | HGF/SF R73E (HP21) | HGF/SF R73E:R76 (HP11) | NK1 (NK1) | NK1 K132E:K134E (1K1) |
|---|---|---|---|---|---|---|---|
| # of cells migrating towards wound | | | | | | | |
| May 23, 2007 set #1 | DHT 0083 p5 | 7 | 24 | 26 | 20 | 22 | 13 |
| May 23, 2007 set #2 | DHT 0083 p5 | 10 | 26 | 30 | 36 | 25 | 14 |
| May 25, 2007 set #1 | DHT 0083 p7 | 14 | 40 | 45 | 24 | 21 | 36 |
| May 25, 2007 set #2 | DHT 0083 p7 | 36 | 58 | 63 | 38 | 35 | 23 |
| May 25, 2007 set #3 | DHT 0083 p7 | 38 | 61 | 44 | 29 | 45 | 42 |
| May 25, 2007 set #4 | DHT 0083 p7 | 27 | 36 | 48 | 59 | 51 | 35 |
| Jun. 18, 2007 set #1 | DHT 0098 p2 | 32 | 57 | 38 | 28 | 47 | 50 |
| Jun. 18, 2007 set #2 | DHT 0098 p2 | 35 | 72 | 56 | 34 | 60 | 60 |
| Jun. 18, 2007 set #3 | DHT 0098 p2 | 40 | 65 | 63 | 70 | 58 | 41 |
| Jun. 27, 2007 set #1 | DHT 0098 p5 | 39 | 56 | 44 | 48 | 50 | 43 |
| Jun. 27, 2007 set #2 | DHT 0098 p5 | 36 | 52 | 40 | 50 | 56 | 30 |
| average | | 28.5 | 49.7 | 45.2 | 39.6 | 42.7 | 35.2 |
| standard deviation | | 12.3 | 15.9 | 12.0 | 15.5 | 14.6 | 14.5 |
| Fold increase in # of cells | | | | | | | |
| May 23, 2007 set #1 | DHT 0083 p5 | 1 | 3.4 | 3.7 | 2.9 | 3.1 | 1.9 |
| May 23, 2007 set #2 | DHT 0083 p5 | 1 | 2.6 | 3.0 | 3.6 | 2.5 | 1.4 |
| May 25, 2007 set #1 | DHT 0083 p7 | 1 | 2.9 | 3.2 | 1.7 | 1.5 | 2.6 |
| May 25, 2007 set #2 | DHT 0083 p7 | 1 | 1.6 | 1.8 | 1.1 | 1.0 | 0.6 |
| May 25, 2007 set #3 | DHT 0083 p7 | 1 | 1.6 | 1.2 | 0.8 | 1.2 | 1.1 |
| May 25, 2007 set #4 | DHT 0083 p7 | 1 | 1.3 | 1.8 | 2.2 | 1.9 | 1.3 |
| Jun. 18, 2007 set #1 | DHT 0098 p2 | 1 | 1.8 | 1.2 | 0.9 | 1.5 | 1.6 |
| Jun. 18, 2007 set #2 | DHT 0098 p2 | 1 | 2.1 | 1.6 | 1.0 | 1.7 | 1.7 |
| Jun. 18, 2007 set #3 | DHT 0098 p2 | 1 | 1.6 | 1.6 | 1.8 | 1.5 | 1.0 |
| Jun. 27, 2007 set #1 | DHT 0098 p5 | 1 | 1.4 | 1.1 | 1.2 | 1.3 | 1.1 |
| Jun. 27, 2007 set #2 | DHT 0098 p5 | 1 | 1.4 | 1.1 | 1.4 | 1.6 | 0.8 |
| average | | 1 | 2.0 | 1.9 | 1.7 | 1.7 | 1.4 |
| standard deviation | | 0 | 0.7 | 0.9 | 0.9 | 0.6 | 0.5 |

It is apparent from the results shown in the above two tables that all of the HGF variants can affect both the migration rate and number of migrating stem cells. All of the proteins produced at least a 1.4 fold increase in migration rate of the stem cells over controls. HP21 had the greatest influence on stem cell migration rate, while 1K1 had the least effect. Table 4 shows that HGF and its variants had a corresponding effect on the number of stem cells found in the wound area. Wild-type HGF had the most significant effect. However, the variants produced notable increases in the number of stem cells found in the wound compared to controls.

Example 4

HP11 and NK1 Mobilize Implanted hCSCs to the Infarct Site in a Mouse Myocardial Infarction Model To examine whether HGF variants could mobilize implanted hCSCs in the MI mouse model, clonogenic EGF-$P^{POS}$-c-kit$^{POS}$-CSCs were injected intramyocardially subsequent to the induction of myocardial infarction by coronary artery occlusion. Subsequently, four injections of IGF-1 and either HP11, HGF, or NK1 were made from the AV-groove to the border zone of the infarct. The concentration of IGF-1 was 200 ng/ml at each of the four sites of injection. Conversely, to create a chemotactic gradient HP11, HGF, or NK1 was injected at increasing concentrations, from the atria to the border zone: 50 ng/ml (AV groove), 100 ng/ml (mid-region) and 200 ng/ml (two opposite sides of the infarct border zone). hCSCs were injected at opposite sites of the border zone and co-injected with rhodamine-labeled microspheres to mark the injection sites. The migration rate was monitored ex vivo by two photon microscopy. The calculated migration rates for the implanted hCSCs that were subsequently mobilized with injections of either HGF and IGF-1 or HP11 and IGF-1 are shown in Table 5. These data suggest that HP11 had a slightly greater effect compared to wild-type HGF on the migration rate of hCSCs towards the damaged tissue.

TABLE 5

Migration of hCSCs implanted in an infracted mouse heart.

| HP11 (R73E, R76E) (SEQ ID NO: 3) | | HGF (SEQ ID NO: 1) | |
|---|---|---|---|
| Expt. date | Migration rate (μm/hr) | Expt. date | Migration rate (μm/hr) |
| Oct. 13, 2006 | | 30-Aug-06 | |
| 1 | 18 | 1 | 24 |
| 2 | 9 | 2 | 12 |
| 3 | 9 | 3 | 24 |
| 4 | 27 | 4 | 36 |
| 5 | 15 | | |
| 6 | 90 | | |
| Average | 28 | Average | 24.0 |
| 19-Oct-06 | | 25-Oct-06 | |
| 1 | 45.5 | 1 | 30 |
| 2 | 53.5 | 2 | 21 |
| 3 | 38 | 3 | 9 |
| 4 | 23 | 4 | 27 |
| 5 | 23 | 5 | 6 |
| Average | 36.6 | Average | 18.6 |
| Sept 6, 06 | | 25-Oct-06 | |
| 1 | 36 | 1 | 28 |
| 2 | 36 | 2 | 44 |

TABLE 5-continued

Migration of hCSCs implanted in an infracted mouse heart.

| HP11 (R73E, R76E) (SEQ ID NO: 3) | | HGF (SEQ ID NO: 1) | |
|---|---|---|---|
| Expt. date | Migration rate (μm/hr) | Expt. date | Migration rate (μm/hr) |
| 3 | 54 | 3 | 51 |
| 4 | 18 | 4 | 43 |
|  |  | 5 | 34 |
|  |  | 6 | 42 |
| Average | 36.0 | Average | 40.3 |
| Overall Average | 33.5 | Overall Average | 27.6 |
| SD | 4.8 | SD | 11.3 |

In a similar experiment, the efficacy of NK1 (SEQ ID NO: 4), the natural splice variant of HGF, to mobilize implanted hCSCs towards the infarct site was examined. EGFP$^{POS}$-c-kit$^{POS}$-CSCs were implanted into the heart of a mouse subsequent to the induction of myocardial infarction. Intramyocardial injections of IGF-1 and NK1 were administered as described above (paragraph 133). The migration of the implanted hCSCs was monitored ex vivo by two photon microscopy. The results of the experiment are depicted in FIG. 1. The three panels (A, B, and C) show different time points after injection of the stem cells (0, 1 hour and 2 hours, respectively). Rhodamine-labeled microspheres (red label) were co-injected with the stem cells to mark the sites of injection. The green label shows the location of the implanted EGFP$^{POS}$ human CSCs. The blue label reveals bundles of collagen fibers. The results show the movement of the implanted human CSCs over time to the infarct site (top right in figure).

Example 5

Figure 2:
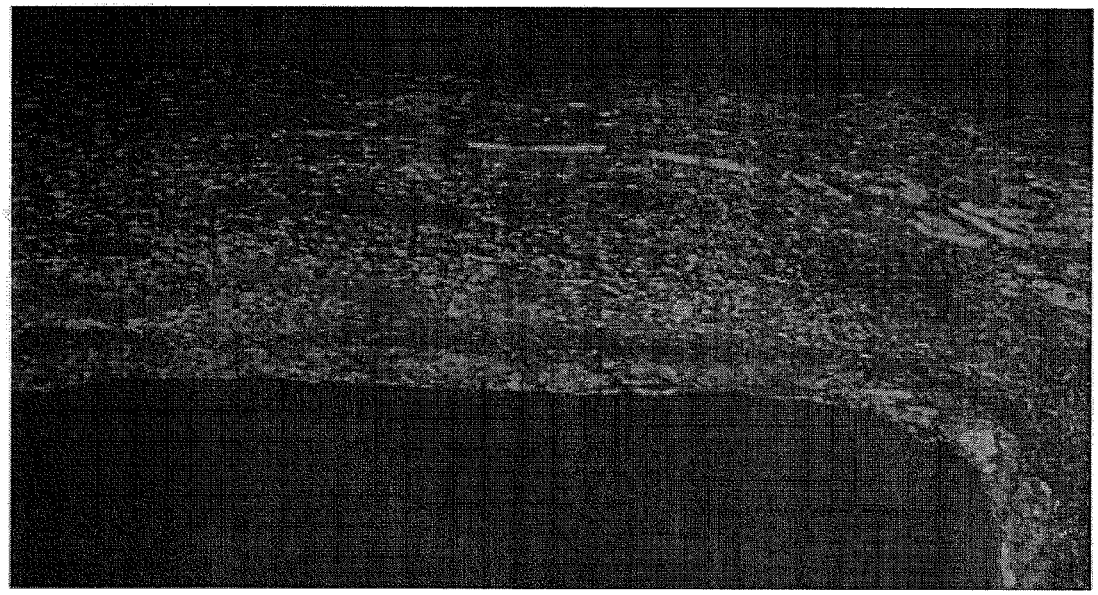
FIG. 2. Myocardial regeneration induced by NK1 and IGF-1 after infarction. Two examples (panels A and B) demonstrating the replacement of a mid-portion of the infarct by a band of regenerated myocytes ten days after coronary artery occlusion and the intramyocardial injection of IGF-1 and NK1. The newly formed myocytes can be identified by the red fluorescence labeling of α-sarcomeric actin. Blue fluorescence corresponds to nuclei stained by DAPI.
Figure 2:
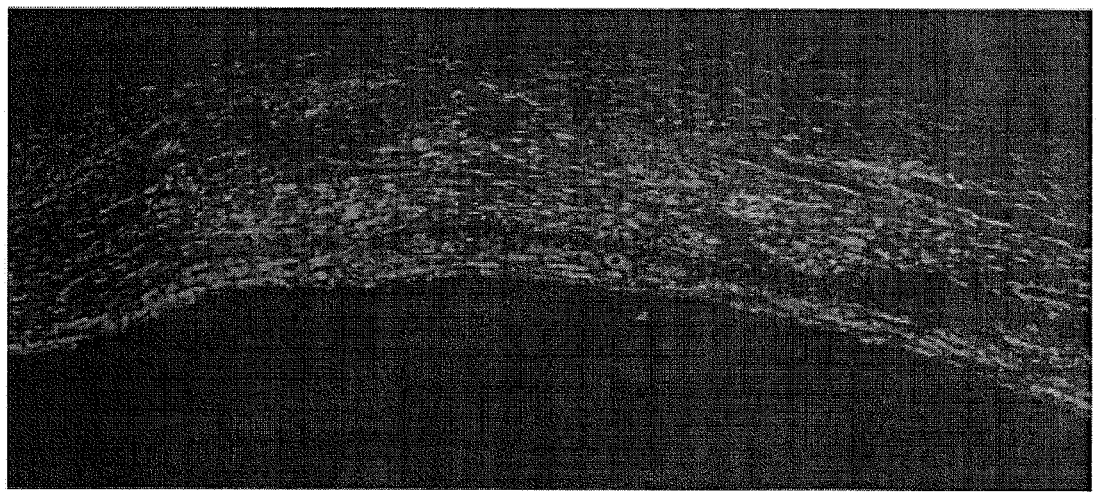

Intramyocardial Injection of NK1 and IGF-1 Induce Myocardial Regeneration after Infarction To examine whether NK1, like its full-length HGF counterpart, could mobilize resident cardiac stem cells to sites of injury, mice were injected with NK1 and IGF-1 subsequent to the induction of myocardial infarction. Myocardial infarction was induced by coronary artery occlusion in female 129 SV-EV mice under ketamine-acepromazine anesthesia. Five hours later, four injections of IGF-1 and NK1 were then made from the AV-groove to the border zone of the infarct. The concentration of IGF-1 was 200 ng/ml at each of the four injection sites. Conversely, a chemotactic gradient of NK1 was created by injecting increasing concentrations of NK1 from the atria to the border zone as follows: 50 ng/ml (AV groove), 100 ng/ml (mid-region), and 200 ng/ml (two opposite sides of the infarct border zone). Ten days after coronary artery occlusion and intramyocardial injection of IGF-1 and NK1, mice were sacrificed and the myocardium was fixed in 10% formalin. Tissues were processed for staining and identification of newly formed myocytes. Newly formed myocytes were labeled with antibodies to α-sacromeric actin. The results of these experiments are shown in FIGS. 2A and B. The figure shows that the mid-portion (panel A) and the subendocardial region (panel B) of the infarct were replaced by a band of regenerated myocytes as indicated by the bright red fluorescence corresponding to α-sacromeric actin. The blue label in the figure shows nuclei stained by DAPI.

Similar experiments were performed using either HGF or 1K1 in place of NK1. Quantitative measurements from this series of experiments comparing the efficacy of intramyocardial injections of IGF-1 combined with either HGF, NK1, or 1K1 are shown below.

| A. Fraction of the infarct replaced by newly formed myocardium. | |
|---|---|
| HGF | 59.9 ± 17.8% (n = 6) |
| NK1 | 61.2 ± 12.7% (n = 8) |
| 1K1 | 52.3 ± 8.9% (n = 8) |
| B. Volume fraction of the new myocardium occupied by myocytes. | |
| HGF | 66.9 ± 14.5% (n = 6) |
| NK1 | 70.4 ± 14.6% (n = 8) |
| 1K1 | 59.3 ± 14.0% (n = 8) |
| C. Cell volume of regenerated myocytes. | |
| HGF | 1,570 ± 300 μm$^3$ (n = 3) |
| NK1 | 1,550 ± 293 μm$^3$ (n = 3) |
| 1K1 | 1,446 ± 224 μm$^3$ (n = 3) |
| D. Number of regenerated myocytes. | |
| HGF | 4.6 ± 2.0 × 10$^6$ (n = 6) |
| NK1 | 4.9 ± 1.9 × 10$^6$ (n = 8) |
| 1K1 | 4.4 ± 1.3 × 10$^6$ (n = 8) |
| E. Length density of arterioles in the new myocardium. | |
| HGF | 29.4 ± 14.2 mm/mm$^3$ (n = 6) |
| NK1 | 35.1 ± 13.4 mm/mm$^3$ (n = 8) |
| 1K1 | 37.1 ± 10.9 mm/mm$^3$ (n = 8) |
| F. Length density of capillaries in the new myocardium. | |
| HGF | 296 ± 86 mm/mm$^3$ (n = 6) |
| NK1 | 312 ± 101 mm/mm$^3$ (n = 8) |
| 1K1 | 271 ± 85 mm/mm$^3$ (n = 8) |

| G. Left ventricular function. | | | | |
|---|---|---|---|---|
|  | LVEDP (mmHg) | LVDevP (mmHg) | +dP/dt (mmHg/s) | +dP/dt (mmHg/s) |
| Sham-operated | 4.7 ± 2.8 | 93.6 ± 7.5 | 9,620 ± 960 | 8,810 ± 1,100 |
| MI-UN | 21.4 ± 2.9 | 60.1 ± 7.0 | 5,010 ± 920 | 4,240 ± 990 |
| MI-HGF | 11.3 ± 7.9* | 82.9 ± 12.1* | 7,850 ± 1,470* | 7,260 ± 1,470* |
| MI-NK1 | 12.5 ± 6.4* | 75.4 ± 11.8* | 7,040 ± 1,490* | 6,400 ± 1,340* |
| MI-1K1 | 11.2 ± 9.8* | 76.5 ± 17.4* | 7,270 ± 1,940* | 6,530 ± 1,720* |

LVEDP, left ventricular end-diastolic pressure;
LVDevP, left ventricular developed pressure;
MI, myocardial infarction;
UN, untreated.
*Indicates significant difference from MI-UN.

These results indicate that NK1 and 1K1 like HGF are capable of mobilizing resident cardiac stem cells to the site of injured tissue where they differentiate into new myocytes to effect structural and functional repair of the infarcted tissue.

Having thus described in detail preferred embodiments of the present invention, it is to be understood that the invention defined by the appended claims is not to be limited by particular details set forth in the above description as many apparent variations thereof are possible without departing from the spirit or scope thereof.

Each of the applications and patents cited in this text, including each of the foregoing cited applications, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, various documents or references are cited in this text, either in a Reference List before the claims or in the text itself, and, each of the documents or references ("herein cited documents") and all of the documents cited in this text (also "herein cited documents"), as well as each document or reference cited in each of the herein cited documents (including any manufacturer's specifications, instructions, etc. for products mentioned herein and in any document incorporated herein by reference), is hereby expressly incorporated herein by reference. There is no admission that any of the various documents cited in this text are prior art as to the present invention. Any document having as an author or inventor person or persons named as an inventor herein is a document that is not by another as to the inventive entity herein. Also, teachings of herein cited documents and documents cited in herein cited documents and more generally in all documents incorporated herein by reference can be employed in the practice and utilities of the present invention.

REFERENCES

1. Abott, J. D. et al. Stromal cell-derived factor-1 alpha plays a critical role in stem cell recruitment to the heart after myocardial infarction but is not sufficient to induce homing in the absence of injury. Circulation 110, 3300-3305 (2004).
2. Aicher, A. et al. Essential role of endothelial nitric oxide synthase for mobilization of stem and progenitor cells. Nat. Med. 9, 1370-1376 (2003).
3. Alvarez-Dolado M, Pardal R, Garcia-Verdugo J M, et al. Fusion of bone-marrow-derived cells with Purkinje neurons, cardiomyocytes and hepatocytes. Nature 2003; 425: 968-73.
4. Amado L C, Saliaris A P, Schuleri K H, et al. Cardiac repair with intramyocardial injection of allogeneic mesenchymal stem cells after myocardial infarction. Proc Natl Acad Sci USA 2005; 102:11474-9.
5. American Heart Association. 2001 Heart and Stroke Statistical Update. Dallas, Tex.: American Heart Association, 2000.
6. American Heart Association: Heart Disease and Stroke Statistics—2005 Update. URL: www.americanheart.org/downloadable/heart/1105390918119HDSStats2005Update.-pdf
7. Anderson, D. J. "Stem cells and pattern formation in the nervous system: the possible versus the actual." Neuron (2001) 30, 19-35.
8. Anversa, P. & Olivetti, G. Cellular basis of physiological and pathological myocardial growth. In Handbook of Physiology: The Cardiovascular System: The Heart. (eds. Page, E., Fozzard, H. A. & Solaro, R. J.) 75-144 (Oxford University Press, Oxford, 2002).
9. Anversa, P. and Kajstura, J. "Ventricular myocytes are not terminally differentiated in the adult mammalian heart." Circ. Res. (1998) 83, 1-14.
10. Anversa, P. and Nadal-Ginard, B., "Myocyte renewal and ventricular remodelling." Nature. (2002); 415(6868):240-3.
11. Arsenijevic, Y. and Weiss, S., J. Neurosci. "Insulin-like growth factor-1 is a differentiation factor for postmitotic CNS stem cell-derived neuronal precursors: distinct actions from those of brain-derived neurotrophic factor." J. Neurosci. (1998) 18(6):2118-28.
12. Arsenijevic, Y. et al., "Insulin-like growth factor-1 is necessary for neural stem cell proliferation and demonstrates distinct actions of epidermal growth factor and fibroblast growth factor-2." J Neurosci. (2001) 21(18):7194-202
13. Asahara, T. et al. Isolation of putative progenitor endothelial cells for angiogenesis. Science 275, 964-967 (1997).
14. Bache, R. J. Effects of hypertrophy on the coronary circulation. Prog. Cardiovasc. Dis. 30, 403-440 (1988).
15. Balsam L B, Wagers A J, Christensen J L, Kofidis T, Weissman I L, Robbins R C. Haematopoietic stem cells adopt mature haematopoietic fates in ischemic myocardium. Nature 2004; 428:668-73.
16. Bautz, F. et al., "Expression and secretion of vascular endothelial growth factor-A by cytokine stimulated hematopoietic progenitor cells. Possible role in the hematopoietic microenvironment." Exp Hematol 2000 June; 28(6):700-6.
17. Baxter, A. G. The cells that knew too much. J. Clin. Invest. 105, 1675 (2000).
18. Beardsle, M. A. et al., "Rapid turnover of connexin43 in the adult rat heart." Circ. Res. (1998) 83, 629-635.
19. Beltrami A P, Barlucchi L, Torella D, et al. Adult cardiac stem cells are multipotent and support myocardial regeneration. Cell 2003; 114:763-76.
20. Beltrami, A. P. et al. "Evidence that human cardiac myocytes divide after myocardial infarction." N Engl J. Med. (2001) 344(23):1750-7.
21. Beltrami, A. P. et al., "Chimerism of the transplanted heart." N Engl J. Med. (2002) 346(1):5-15.
22. Beltrami, A. P. et al., Submitted (2002).
23. Beltrami, C. A. et al., "Structural basis of end-stage failure in ischemic cardiomyopathy in humans." Circulation (1994) 89, 151-163.
24. Bianco, P. et al. "Bone marrow stromal stem cells: nature, biology, and potential applications." Stem Cells (2001) 19:180-192.
25. Birchmeier, C. and Brohmann, H., Curr. Opin. Cell Biol. 12, 725 (2001).
26. Blackstone, E. H. & Lytle, B. W. Competing risks after coronary bypass surgery: the influence of death on reintervention. J. Thorac. Cardiovasc. Surg. 119, 1221-1230 (2000).
27. Blanpain C, Lowry W E, Geoghegan A, Polak L, Fuchs E. Self-renewal, multipotency, and the existence of two cell populations within an epithelial stem cell niche. Cell 2004; 118:63 5-48.
28. Blau, H. M. et al., "The evolving concept of a stem cell: entity or function?" Cell. (2001);105(7):829-4 1.
29. Block, G. D. et al., J. Cell Biol. 132, 1133 (1996).
30. Blume et al., "A review of autologous hematopoetic cell transplantation." Biology of Blood & Marrow Transplantation, (2000) 6: 1-12.
31. Bodine, D. M. et al., "Efficient retrovirus transduction of mouse pluripotent hematopoietic stem cells mobilized into the peripheral blood by treatment with granulocyte colony-stimulating factor and stem cell factor." Blood (1994) 84, 1482-1491.
32. Breier, G. et al., "Molecular cloning and expression of murine vascular endothelial-cadherin in early stage development of cardiovascular system." Blood (1996) 87, 630-641.
33. Britten, M. B. et al. Infarct remodeling after intracoronary progenitor cell treatment in patients with acute myocardial infarction (TOPCARE-AMI): mechanistic insights from serial contrast-enhanced magnetic resonance imaging. Circulation 108, 2212-2218 (2003).
34. Brooker, G. J. et al., "Endogenous IGF-1 regulates the neuronal differentiation of adult stem cells." J Neurosci Res. (2000) 59(3):332-41.
35. Broudy, V. C. "Stem cell factor and hematopoiesis." Blood (1997) 90, 1345-1364.

36. Brugger et al., "Ex vivo manipulation of hematopoetic stem and progenitor cells. Seminars in Hematology." (2000), 37 (1): 42-49.
37. Bunting, K. D. et al., Blood 96, 902 (2000).
38. Butler, J. M. et al. SDF-1 is both necessary and sufficient to promote proliferative retinopathy. J. Clin. Invest. 115, 86-93 (2005).
39. Caceres-Cortes, J. R. et al., "Steel factor sustains SCL expression and the survival of purified CD34+ bone marrow cells in the absence of detectable cell differentiation." Stem Cells (2001) January; 19(1):59-70.
40. Capasso, J. M. and Anversa, P., Am. J. Physiol. 263, H841 (1992).
41. Caplan A. I. and Haynesworth S. E., "Method for enhancing the implantation and differentiation of marrow-derived mesenchymal cells." Filed Nov. 16, 1990. U.S. Pat. No. 5,197,985
42. Carmeliet, P. Angiogenesis in life, disease and medicine. Nature 438, 932-936 (2005).
43. Ceradini, D. J. & Gurtner G. C. Homing to hypoxia: HIF-1 as a mediator of progenitor cell recruitment to injured tissue. Trends Cardiovasc. Med. 15, 57-63 (2005).
44. Ceradini, D. J. et al. Progenitor cell trafficking is regulated by hypoxic gradients through HIF-1 induction of SDF-1. Nat. Med. 10, 858-864 (2004).
45. Cheng, W. et al. "Aging does not affect the activation of the myocyte IGF-1 autocrine system after infarction and ventricular failure in Fischer 344 rats." Circ. Res. (1996) 78, 536-546.
46. Chien K R. Stem cells: lost in translation. Nature 2004; 428:607-8.
47. Chimenti C, Kajstura J, Torella D, et al. Senescence and death of primitive cells and myocytes lead to premature cardiac aging and heart failure. Circ Res 2003; 93:604-13.
48. Chiu et al., "Cellular Cardiomyoplasty: Myocardial Regeneration With Satellite Cell Implantation." Ann. Thorac. Surg. (1995) 60: 12-18.
49. Cleutjens, J. P. M., Blankesteijn, W. M., Daemen, M. J. A. P. & Smits, J. F. M. The infarcted myocardium: Simply dead tissue, or a lively target for therapeutic interventions. Cardiovasc. Res. 44, 232-241 (1999).
50. Clutterbuck, R. D. et al., "G-CSF mobilization of haemopoietic cell populations in SCID mice engrafted with human leukaemia." Bone Marrow Transplant (1997) August; 20(4):325-32.
51. Coles, J. G. et al., "Inhibition of Human Xenogenic or Allogenic Antibodies to Reduce Xenograft or Allograft Rejection in Human Recipients". Patent No. WO 95/34581A1, published Dec. 21, 1995.
52. Condorelli, G. et al., "Cardiomyocytes induce endothelial cells to trans-differentiate into cardiac muscle: implications for myocardium regeneration." Proc Natl Acad Sci USA. (2001) 98(19): 10733-8.
53. Coultas, L., Chawengsaksophak, K. & Rossant, J. Endothelial cells and VEGF in vascular development. Nature 438, 937-945 (2005).
54. Couper, L. L. et al., "Vascular endothelial growth factor increases the mitogenic response to fibroblast growth factor-2 in vascular smooth muscle cells in vivo via expression of fms-like tyrosine kinase-1." (1997) Circ. Res. 81, 932-939.
55. Dang N C, Johnson C, Eslami-Farsani M, Haywood L J. Bone marrow embolism in sickle cell disease: a review. Am J Hematol 2005; 79:61-7.
56. Dawn, B. et al. Cardiac stem cells delivered intravascularly traverse the vessel barrier, regenerate infarcted myocardium, and improve cardiac function. Proc. Natl. Acad. Sci. USA 102, 3766-3771 (2005).
57. Development." (1993) Development 118(2), 489-498.
58. Dinsmore, J. "Procine Cardiomyocytes and Their Use in Treatment of Insufficient Cardiac Function". Patent No. WO 96/38544, published Dec. 5, 1996.
59. Durocher, D. et al., "The cardiac transciption factors Nkx2-5 and GATA-4 are mutual cofactors." EMBO J. 16, 5687-5696 (1997).
60. Eisenberg, C. A & Bader, D. "QCE-6: a clonal cell line with cardiac myogenic and endothelial cell potentials." Dev. Biol. (1995) 167, 469-481.
61. Field L. J. "Myocardial grafts and cellular compositions." Filed Jun. 7, 1995. U.S. Pat. No. 5,733,727.
62. Field L. J. "Non-human mammal having a graft and methods of delivering protein to myocardial tissue." Filed Nov. 16, 1992. U.S. Pat. No. 5,602,301.
63. Field, L. J. "Myocardial Grafts and Cellular Compositions Useful for Same." Patent No. WO 95/14079A1, published May 26, 1995.
64. Fielding et al., "Autologous bone marrow transplantation." Curr. Opin. Hematology, 1994, 1: 412-417.
65. Fishbein, M. C., Maclean, D. & Maroko, P. R., Experimental myocardial infarction in the rat: qualitative and quantitative changes during pathologic evolution. Am. J. Pathol. 90, 57-70 (1978).
66. Frisch, S. M. & Screaton, R. A. Anoikis mechanisms. Curr. Opin. Cell Biol. 5, 555-562 (2001).
67. Gillis S. "Method for improving autologous transplantation." Filed Sep. 26, 1991. U.S. Pat. No. 5,199,942
68. Gritti, A. et al. "Epidermal and fibroblast growth factors behave as mitogenic regulators for a single multipotent stem cell-like population from the subventricular region of the adult mouse forebrain." J. Neurosci. (1999) 19, 3287-3297.
69. Gussoni et al., "Normal dystrophin transcripts detected in Duchenne muscular dystrophy patients after myoblast transplantation." Nature 356:435-438 (1992).
70. Hamasuna, R. et al. "Regulation of matrix metalloproteinase-2 (MMP-2) by hepatocyte growth factor/scatter factor (HGF/SF) in human glioma cells: HGF/SF enhances MMP-2 expression and activation accompanying up-regulation of membrane type-1 MMP." Int J Cancer. (1999) 82(2):274-81.
71. Helmchen, F. & Denk, W. Deep tissue two-photon microscopy. Nat. Methods 2, 932-940 (2005).
72. Hermann, H. and Aebi, U. "In Subcellular Biochemistry: Intermediate Filaments." Vol. 31 (ed. Herrmann, H. & Harris, E.) 319-362 (Plenum Press, New York, 1998).
73. Hidemasa, O. et al. "Telomerase reverse transcriptase promotes cardiac muscle cell proliferation, hypertrophy, and survival." Proc. Natl. Acad. Sci. USA 98, 10308-10313 (2001).
74. Hillebrands, J-L. et al. "Origin of neointimal endothelium and .alpha.-actin-positive smooth muscle cells in transplant arteriosclerosis." J. Clin. Invest. (2001) 107, 1411-1422.
75. Huang H. M. et al., "Optimal proliferation of a hematopoietic progenitor cell line requires either costimulation with stem cell factor or increase of receptor expression that can be replaced by overexpression of Bcl-2. Blood." 1999 Apr. 15; 93(8):2569-77.
76. Ikuta, K. et al., "Mouse hematopoietic stem cells and the interaction of c-kit receptor and steel factor." International Journal of Cell Cloning 1991; 9:451-460.

77. Jackson, K. A. et al., "Hematopoietic potential of stem cells isolated from murine skeletal muscle." Proc Natl Acad Sci USA. (1999) 96(25):14482-6.
78. Jackson, K. A. et al., J. Clin. Invest. (2001) 107, 1395.
79. Janowska-Wieczorek, A. et al., "Autocrine/paracrine mechanisms in human hematopoiesis." Stem Cells 2001; 19:99-107.
80. Jessup, M. & Brozena, S. Heart failure. N. Engl. J. Med. 348, 2007-2018 (2003).
81. Jo, D. Y. et al., "Chemotaxis of primitive hematopoietic cells in response to stromal cell-derived factor-1." The Journal of Clinical Investigation 2000 January; 105(1): 101-111.
82. Just L, Timmer M, Tinius J, et al. Identification of human cells in brain xenografts and in neural co-cultures of rat by in situ hybridisation with Alu probe. J Neurosci Methods 2003; 126:69-77.
83. Kachinsky, A. M. et al., "Intermediate filaments in cardiac myogenesis: nestin in the developing mouse heart." (1995) J. Histochem. Cytochem. 43, 843-847.
84. Kajstura J, Rota M, Whang B, et al. Bone marrow cells differentiate in cardiac cell lineages after infarction independently of cell fusion. Circ Res 2005; 96:127-37.
85. Kajstura, J. et al. "Apoptotic and necrotic myocyte cell deaths are independent contributing variables of infarct size in rats." Lab. Invest. (1996) 74, 86-107.
86. Kajstura, J. et al., "The cellular basis of pacing-induced dilated cardiomyopathy. Myocyte cell loss and myocyte cellular reactive hypertrophy." (1995) Circulation 92, 2306-2317.
87. Kanj et al., "Myocardial ischemia associated with high-dose carmustine infusion." Cancer, 1991, 68 (9): 1910-1912.
88. Kasahara, H. et al., "Cardiac and extracardiac expression of Csx/Nkx2.5 homeodomain protein." (1998) Circ. Res. 82, 936-946.
89. Kawada H, Fujita J, Kinjo K, et al. Nonhematopoietic mesenchymal stem cells can be mobilized and differentiate into cardiomyocytes after myocardial infarction. Blood 2004; 104:3581-87.
90. Kawamoto A, Tkebuchava T, Yamaguchi J, et al. Intramyocardial transplantation of autologous endothelial progenitor cells for therapeutic neovascularization of myocardial ischemia. Circulation 2003; 107:461-8.
91. Kedes, L. H. et al., "Compositions and Methods for Transduction of Cells." Patent No. WO 95/12979A1, published May 18, 1995.
92. Kehat, I. et al. "Human embryonic stem cells can differentiate into myocytes with structural and functional properties of myocytes." J. Clin. Invest. (2001) 108, 407-414.
93. Keil F. et al., "Effect of interleukin-3, stem cell factor and granulocyte-macrophage colony-stimulating factor on committed stem cells, long-term culture initiating cells and bone marrow stroma in a one-step long-term bone marrow culture." Ann Hematol. 2000 May; 79(5):243-8.
94. Kempermann, G. et al., "Activity-dependent regulation of neuronal plasticity and self repair." Prog Brain Res 2000; 127:35-48.
95. Kim, C. H. and Broxmeyer H. E., "In vitro behavior of hematopoietic progenitor cells under the influence of chemoattractants: stromal cell-derived factor-1, steel factor, and the bone marrow environment." Blood 1998 Jan. 1; 91(1):100-10.
96. Kocher, A. A. et al., "Neovascularization of ischemic myocardium by human bone-marrow-derived angioblasts prevents cardiomyocyte apoptosis reduces remodeling and improves cardiac function." Nature Medicine 2001 April; 7(4):430-436.
97. Koh et al., "Differentiation and long-term survival of C2C12 myoblast grafts in heart." Journal of Clinical Investigation 92:1548-1554 (1993).
98. Krause, D. S. et al., "Multi-organ, multi-lineage engraftment by a single bone marrow-derived stem cell." Cell (2001) May; 105(3)369-370.
99. Kronenwett, R. et al., "The role of cytokines and adhesion molecules for mobilization of peripheral blood stem cells." Stem Cells 2000; 18:320-330.
100. LaIuppa, J. A. et al., "Evaluation of cytokines for expansion of the megakaryocyte and ranulocyte lineages." Stem Cells (1997) May: 15(3):198-206.
101. Lanza R, Moore M A, Wakayama T, et al. Regeneration of the infarcted heart with stem cells derived by nuclear transplantation. Circ Res 2004; 94:820-7.
102. Lapidot, T., Dar, A. & Kollet, O. How do stem cells find their way home? Blood 106, 1901-1910 (2005).
103. Lee, J. Y. et al. "Clonal isolation of muscle-derived cells capable of enhancing muscle regeneration and bone healing." J. Cell Biol. (2000) 150, 1085-1099.
104. Leong F T, Freeman L J. Acute renal infarction. JR Soc Med 2005; 98:121-2.
105. Leor et al., "Transplantation of Fetal Myocardial Tissue Into the Infarcted Myocardium of Rat, A Potential Method for Repair of Infarcted Myocardium?" Circulation 94: (Supplement II) II-332-II-336 (1996).
106. Leri A, Kajstura J, Anversa P. Cardiac stem cells and mechanisms of myocardial regeneration. Physiol Rev 2005; 85:1373-416.
107. Leri A, Kajstura J, Anversa P. Identity deception: not a crime for a stem cell. Physiology (Bethesda) 2005; 20:162-8.
108. Leri, A. et al., Circ. Res. 84, 752 (1999).
109. Li et al., "Method of Culturing Cardiomyocytes from Human Pediatric Ventricular Myocardium." (1992) J. Tiss. Cult. Meth.; 93-100.
110. Li et al., "In Vivo Survival and Function of Transplanted Rat Cardiomyocytes" Circulation Research 78:283-288 (1996).
111. Li et al., "Cardiomyocyte Transplantation Improves Heart Function" (1996) The Society of Thoracic Surgeons; 62: 654-661.
112. Li et al., "Human Pediatric and Adult Ventricular Cardiomyocytes in Culture: Assessment of Phenotypic Changes with Passaging" Feb. 20, 1996 Cardiovascular Research; 1-12.
113. Li et al., Cardiovascular Res. 32:362-373 (1996).
114. Li et al., J. Mol. Cell. Cardiol., 26:A162 (1994).
115. Li, B et al., "Insulin-like growth factor-1 attenuates the detrimental impact of nonocclusive coronary artery constriction on the heart." (1999) Circ. Res. 84, 1007-1019.
116. Li, P. et. al. "Myocyte performance during evolution of myocardial infarction in rats: effects of propionyl-L-carnitine." Am. J. Physiol. (1995) 208, H1702-H1713.
117. Li, Q. et al. "Overexpression of insulin-like growth factor-1 in mice protects from myocyte death after infarction, attenuating ventricular dilation, wall stress, and cardiac hypertrophy." J Clin Invest. 100, 1991-1999 (1997).
118. Lin, Q. et al., "Control of mouse cardiac morphogenesis and myogenesis by transcription factor MEF2C." (1997) Science 276, 1404-1407.
119. Linke A, Muller P, Nurzynska D, et al. Stem cells in the dog heart are self-renewing, clonogenic, and multipotent and regenerate infarcted myocardium, improving cardiac function. Proc Natl Acad Sci USA 2005; 102:8966-71.
120. Lopez L R, Schocket A L, Stanford R E, Claman H N, Kohler P F. Gastrointestinal involvement in leukocytoclastic vasculitis and polyarteritis nodosa. J Rheumatol 1980; 7:677-84.
121. MacLellan, W. R. and Schneider, M. D. "Genetic dissection of cardiac growth control pathways." Annu. Rev. Physiol. (2000) 62, 289-319.
122. Malouf, N. N. et al., "Adult derived stem cells from the liver become myocytes in the heart in vivo." Am J Pathology 2001 June; 158(6)1929-35.
123. Matsuura K, Nagai T, Nishigaki N, et al. Adult cardiac Sca-1-positive cells differentiate into beating cardiomyocytes. J Biol Chem 2004; 279:11384-91.
124. Maude G H. Bone marrow infarction in sickle cell anemia. Blood 1984; 63:243.
125. Melendez, J. et al. Cardiomyocyte apoptosis triggered by RAFTK/pyk2 via src kinase is antagonized by Paxillin. J. Biol. Chem. 279, 53516-53523 (2004).
126. Menasche, P. et al., (2000) Lancet 357, 279-280.
127. Messina E, De Angelis L, Frati G. et al. Isolation and expansion of adult cardiac stem cells from human and murine heart. Circ Res 2004; 95:911-21.
128. Mikawa, T. & Fishman, D. A. "The polyclonal origin of myocyte lineages." Annu. Rev. Physiol. (1996) 58, 509-521.
129. Mohr A, Zwacka R M, Jarmy G, et al. Caspase-8L expression protects CD34+ hematopoietic progenitor cells and leukemic cells from CD95-mediated apoptosis. Oncogene 2005; 24:2421-9.
130. Monga, S. P. et al. "Expansion of hepatic and hematopoietic stem cells utilizing mouse embryonic liver explants." (2001) Cell Transplant. January-February; 10(1), 81-89.
131. Morin, S. et al., "GATA-dependent recruitment of MEF2 proteins to target promoters." (2000) EMBO J. 19, 2046-2055.
132. Mouquet, F. et al. Restoration of cardiac progenitor cells after myocardial infarction by self-proliferation and selective homing of bone marrow-derived stem cells. Circ. Res. 97, 1090-1092 (2005).
133. Murray et al., "Skeletal Myobalst Transplantation for Repair of Myocardial Necrosis" J. Clin. Invest. 98:2512-2523 (1996).
134. Murry C E, Soonpaa M H, Reinecke H, et al. Haematopoietic stem cells do not transdifferentiate into cardiac myocytes in myocardial infarcts. Nature 2004; 428:664-8.
135. Musil, L. S. et al., "Regulation of connexin degradation as a mechanism to increase gap junction assembly and function." (2000) J. Biol. Chem. 275, 25207-25215.
136. Nakamura T, Schneider M D. The way to a human's heart is through the stomach: visceral endoderm-like cells drive human embryonic stem cells to a cardiac fate. Circulation 2003; 107:2638-9.
137. National Institutes of Health. "Stem Cells: A Primer." National Institutes of Health: May 2000.
138. Noishiki et al., "Angiogenic growth factor release system for in vivo tissue engineering: a trial of bone marrow transplantation into ischemic myocardium." (1999) J. Artif. Organs, 2: 85-91.
139. Nygren J M, Jovinge S, Breitbach M, et al. Bone marrow-derived hematopoietic cells generate cardiomyocytes at a low frequency through cell fusion, but not transdifferentiation. Nat Med 2004; 10:494-501.
140. Oh H, Bradfute S B, Gallardo T D, et al. Cardiac progenitor cells from adult myocardium: homing, differentiation, and fusion after infarction. Proc Natl Acad Sci USA 2003; 100:123 13-8.
141. Olivetti, G. et al., "Cellular basis of chronic ventricular remodeling after myocardial infarction in rats." (1991) Circ. Res. 68(3), 856-869.
142. Olivetti, G., Anversa, P. & Loud, A. V. Morphometric study of early postnatal development in the left and right ventricular myocardium of the rat. II. Tissue composition, capillary growth, and sarcoplasmic alterations. Circ. Res. 46, 503-512 (1980).
143. Orlic D, Kajstura J, Chimenti S, et al. Bone marrow cells regenerate infarcted myocardium. Nature 2001; 410:701-5.
144. Orlic, D. et al., (1993) Blood 91, 3247-3254.
145. Orlic, D. et al., "Mobilized bone marrow cells repair the infarcted heart, improving function and survival." Proc Natl Acad Sci USA. (2001) 98(18):10344-9.
146. Page, D. L. et al., "Myocardial changes associated with cardiogenic shock." N Engl J. Med. (1971) 285(3):133-7.
147. Pasumarthi, K. B. S. et al., "Coexpression of mutant p53 and p193 renders embryonic stem cell-derived cardiomyocytes responsive to the growth-promoting activities of adenoviral EIA." Circ Res. (2001) 88(10):1004-11.
148. Patchen, M L et al. "Mobilization of peripheral blood progenitor cells by Betafectin.® PGG-glucan alone and in combination with granulocyte colony-stimulating factor." Stem Cells (1998) May; 16(3):208-217.
149. Patel, A. N., et al., "Surgical treatment for congestive heart failure with autologous adult stem cell transplantation: A prospective randomized study." The Journal of Thoracic and Cardiovascular Surgery (2005) December; 130 (6):1631-38.
150. Perrin, E. C., et al., "Transendocardial autologous bone marrow cell transplantation for severe, chronic ischemic heart failure." Circulation (2003); 107:2294-2302.
151. Pfeffer, M. A. and Braunwald, E. "Ventricular remodeling after myocardial infarction." Circulation 81, 1161-1172 (1990).
152. Pfister O, Mouquet F, Jain M, et al. CD31− but not CD31+ cardiac side population cells exhibit functional cardiomyogenic differentiation. Circ Res 2005; 97:52-61.
153. Pollick, C. et al., "Echocardiographic and cardiac Doppler assessment of mice." (1995) J. Am. Soc. Echocardiogr. 8, 602-610 (1995).
154. Powell, E. M. et al., Neuron. 30, 79 (2001).
155. Quaini, F. et al. "Chimerism of the transplanted heart." (2002) N Engl J. Med. 346(1):5-15 N.
156. Rakusan K, Flanagan M F, Geva T, Southern J, Van Praagh R. Morphometry of human coronary capillaries during normal growth and the effect of age in left ventricular pressure-overload hypertrophy. Circulation 1992; 86:38-46.
157. Rakusan, K. Cardiac growth, maturation, and aging. In Growth of the Heart in Health and Disease (ed Zak, R.) 131-164 (Raven Press, New York, 1984).
158. Rao, M. S, and Mattson, M. P. "Stem cells and aging: expanding the possibilities. Mech. Ageing Dev. (1998) 122, 713-734.
159. Rappolee, D. A. et al., Circ. Res. 78, 1028 (1996).
160. Reiss, K. et al., "Overexpression of insulin-like growth factor-1 in the heart is coupled with myocyte proliferation in transgenic mice." (1996) Proc. Natl. Acad. Sci. USA 93(16), 8630-8635.
161. Reya, T. et al., "Stem cells, cancer, and cancer stem cells." (2001) Nature 414(6859):105-11.

162. Roberts M. M., et al., "Prolonged release and c-kit expression of haemopoietic precursor cells mobilized by stem cell factor and granulocyte colony stimulating factor." Br J Haematol. 1999 March; 104(4):778-84.
163. Rosenthal, N. and Tsao, L. "Helping the heart to heal with stem cells." Nature Medicine 2001 April; 7(4):412-413.
164. Rossi D J, Bryder D, Zahn J M, et al. Cell intrinsic alterations underlie hematopoietic stem cell aging. Proc Natl Acad Sci USA 2005; 102:9194-9.
165. Saegusa M, Takano Y, Okudaira M. Human hepatic infarction: histopathological and postmortem angiological studies. Liver 1993; 13:239-45.
166. Sanderson, W. C. & Scherbov, S. Average remaining lifetimes can increase as human populations age. Nature 435, 811-813 (2005).
167. Schenke-Layland, K., Riemann, I., Stock, U. A. & Konig, K. Imaging of cardiovascular structures using near-infrared femtosecond multiphoton laser scanning microscopy. J. Biomed. Opt. 10, 024017 (2005).
168. Scholzen, T., and Gerdes, J. "The ki-67 protein: from the known and the unknown." J. Cell. Physiol. 182, 311-322 (2000).
169. Seale, P. et al. "Pax7 is required for the specification of myogenic satellite cells." Cell (2000) 102, 777-786.
170. Sherman, W. "Cellular therapy for chronic myocardial disease: nonsurgical approaches." Basic Appl. Myol. (2003); 13(1): 11-14.
171. Shihabuddin, L. S. et al., "Adult spinal cord stem cells generate neurons after transplantation in the adult dentate gyrus." J. Neurosci. (2000) 20, 8727-8735.
172. Shimomura T., et al., "Thrombopoietin stimulates murine lineage negative, Sca-1+, C-Kit+, CD34-cells: comparative study with stem cell factor or interleukin-3." Int J Hematol. (2000) January; 71(1):33-9.
173. Silver J. et al., "Methods of reducing glial scar formation and promoting axon and blood vessel growth and/or regeneration through the use of activated immature astrocytes." Filed Oct. 27, 1989. U.S. Pat. No. 5,202,120.
174. Simnett et al. "Autologous stem cell transplantation for malignancy: a systemic review of the literature." Clin. Lab Haem. 2000, 22:61-72.
175. Smith D. A. and Townsend L E. "Method of isolation, culture and proliferation of human atrial myocytes." Filed Sep. 21, 1995. U.S. Pat. No. 5,543,318
176. Smith D. A. et al., "Method for inducing human myocardial cell proliferation." Filed Apr. 4, 1995. U.S. Pat. No. 5,580,779
177. Soonpaa et al. "Formation of nascent intercalated disks between grafted fetal cardiomyocytes and host myocardium." (1994) Science 264(5155):98-101.
178. Stainer, D. Y. R. et al., "Cardiovascular development in zebrafish. I. Myocardial fate and heart tube formation." Development (1993) 119, 31-40.
179. Strobel, E S et al. "Adhesion and migration are differentially regulated in hematopoietic progenitor cells by cytokines and extracellular matrix." Blood (1997) Nov. 1; 90(9): 3524-3532.
180. Taylor, D. A. et al. (1998) Nature Med. 4, 929-933.
181. Temple, S. "Opinion: Stem cell plasticity—building the brain of our dreams." Nat Rev Neurosci 2001 July; 2(7): 513-520.
182. Terada, N. et al. Nature, Advanced online publication DOI: nature730, (2002).
183. Thompson et al. Science 257:868-870 (1992).
184. Tomita, S et al. (1999) Circulation 100(suppl II), II-247-II-256.
185. Tropepe, V. et al. "Distinct neural stem cells proliferate in response to EGF and FGF developing mouse telencephalon." Dev. Biol. (1999) 208, 166-188.
186. Urbanek K, Rota M, Cascapera S, et al. Cardiac stem cells possess growth factor-receptor systems that after activation regenerate the infarcted myocardium, improving ventricular function and long-term survival. Circ Res 2005; 97:663-73.
187. Urbanek K, Quaini F, Tasca G, et al. Intense myocyte formation from cardiac stem cells in human cardiac hypertrophy. Proc Natl Acad Sci USA 2003; 100:10440-5.
188. Urbanek K, Torella D, Sheikh F, et al. Myocardial regeneration by activation of multipotent cardiac stem cells in ischemic heart failure. Proc Natl Acad Sci USA 2005; 102:8692-7.
189. Urbich C, Dimmeler S. Endothelial progenitor cells: characterization and role in vascular biology. Circ Res 2004; 95:343-53.
190. Vassilopoulos G, Wang P R, Russell D W. Transplanted bone marrow regenerates liver by cell fusion. Nature 2003; 422:901-4.
191. Vaughn et al. "Incorporating bone marrow transplantation into NCCN guidelines." (1998) Oncology, 12 (11A): 390-392.
192. Wagers, A. J. & Weissman, I. L. Plasticity of adult stem cells. Cell 116, 639-648 (2004).
193. Wang X, Willenbring H, Akkari Y, et al. Cell fusion is the principal source of bone-marrow-derived hepatocytes. Nature 2003; 422:897-901.
194. Wang, H. and Keiser, J. A., "Hepatocyte growth factor enhances MMP activity in human endothelial cells." Biochem Biophys Res Commun. 2000; 272(3):900-5.
195. Watanabe K, Abe H, Mishima T, Ogura G, Suzuki T. Polyangitis overlap syndrome: a fatal case combined with adult Henoch-Schonlein purpura and polyarteritis nodosa. Pathol Int 2003; 53:569-73.
196. Weimann J M, Johansson C B, Trejo A, Blau H M. Stable reprogrammed heterokaryons form spontaneously in Purkinje neurons after bone marrow transplant. Nat Cell Biol 2003; 5:959-66.
197. Weimar, I. S. et al., "Hepatocyte growth factor/scatter factor (HGF/SF) is produced by human bone marrow stromal cells and promotes proliferation, adhesion and survival of human hematopoietic progenitor cells (CD34+)." Exp Hematol. (1998) 26(9):885-94.
198. Xing, X. et al., Am. J. Pathol. 158, 1111 (2001).
199. Yamaguchi, T. P. et al., "Flk-1, an flt-related receptor tyrosine kinase is an early marker for endothelial cell precursors.
200. Ying, Q-L. et al., Nature, Advanced online publication DOI: nature729, (2002).
201. Yoon Y S, Wecker A, Heyd L, et al. Clonally expanded novel multipotent stem cells from human bone marrow regenerate myocardium after myocardial infarction. J Clin Invest 2005; 1 5:326-38.
202. Yu, C. Z. et al., Stem Cells 16, 66 (1998).
203. Zaucha, J. M. et al. "Hematopoietic responses to stress conditions in young dogs compared with elderly dogs." Blood (2001) 98, 322-327.
204. Zimmermann W H, Didie M, Wasmeier G H, et al. Cardiac grafting of engineered heart tissue in syngeneic rats. Circulation 2002; 106:1151-7.
205. Ko, S H et al., J Biol chem. 2006 (epub ahead of print)
206. Kanemura Y et al, Cell Transplant. 14:673-682, 2005
207. Kaplan R N et al, Nature 438:750-751, 2005
208. Xu R H, Methods Mol. Med. 121:189-202, 2005
209. Quinn J et al, Methods Mol. Med. 121:125-148, 2005

210. Almeida M et al, J Biol. Chem. 280:41342-41351, 2005
211. Barnabe-Heider F et al, Neuron 48:253-265, 2005
212. Madlambayan G J et al, Exp Hematol 33:1229-1239, 2005
213. Kamanga-Sollo E et al, Exp Cell Res 311:167-176, 2005
214. Heese O et al, Neuro-oncol. 7:476-484, 2005
215. He T et al, Am J. Physiol. 289:H968-H972, 2005
216. Beattie G M et al, Stem Cells 23:489-495, 2005
217. Sekiya I et al, Cell Tissue Res 320:269-276, 2005
218. Weidt C et al, Stem Cells 22:890-896, 2004
219. Encabo A et al, Stem Cells 22:725-740, 2004
220. Buytaeri-Hoefen K A et al, Stem Cells 22:669-674, 2004
221. Schmidt, C. et al. (1995) Scatter factor/hepatocyte growth factor is essential for liver development. Nature 373: 699-702.
222. Bottaro, D. P. et al. (1991) Identification of the hepatocyte growth factor receptor as the c-met proto-oncogene product. Science 251: 802-804.
223. Bladt et al. (1995) Essential role for the c-met receptor in the migration of myogenic precursor cells into the limb bud. Nature 376: 768-71.
224. Caton et al. (2000) The branchial arches and HGF are growth-promoting and chemoattractant for cranial motor axons. Development 127: 1751-66.
225. Ebens et al (1996) Hepatocyte growth factor/scatter factor is an axonal chemoattractant and a neurotrophic factor for spinal motor neurons. Neuron 17: 1157-72.
226. Cioce, V., et al. (1996) Hepatocyte growth factor (HGF)/NK1 is a naturally occurring HGF/scatter factor variant with partial agonist/antagonist activity. J. Biol. Chem. 271: 13110-13115.
227. Donate, L. E. et al. (1994) Molecular evolution and domain structure of plasminogen-related growth factors (HGF/SF and HGF1/MSP). Protein Sci. 3: 2378-2394.
228. Jakubczak, J. L. et al. (1998) NK1, a natural splice variant of hepatocyte growth factor/scatter factor, is a partial agonist in vivo. Mol. Cell. Biol. 18: 1275-1283.
229. Miyazawa, K. et al. (1991) An alternatively processed mRNA generated from human hepatocyte growth factor gene. Eur. J. Biochem. 197: 15-22.
230. Gherardi et al. Variants of the NK1 fragment of hepatocyte growth factor/scatter factor (HGF/SF) and their use. Filed Apr. 29, 2002. U.S. Pat. No. 7,179,786.
231. Lietha, D. et al. (2001) Crystal structures of NK1-heparin complexes reveal the basis for NK1 activity and enable engineering of potent agonists of the MET receptor. EMBO Journal 20: 5543-5555.
232. Hartmann, G. et al. (1998) Engineered mutants of HGF/SF with reduced binding to heparan sulphate proteoglycans, decreased clearance and enhanced activity in vivo. Current Biology. 8:125-34.

The invention claimed is:

1. A method for restoring functional and structural integrity to damaged myocardium in a subject in need thereof, the method comprising administering to the subject an effective amount of at least one variant of hepatocyte growth factor selected from the group consisting of NK1, 1K1, 1K2, HP11, HP12, and HP21 to form a chemotactic gradient in the subject's heart sufficient to cause adult cardiac stem cells resident in the heart to replicate and migrate to the area of the damaged myocardium, wherein the functional and structural integrity of the damaged myocardium is restored following the migration of adult cardiac stem cells to the area of damaged myocardium.

2. The method of claim 1, wherein said stem cells are c-kit$^{Pos}$.

3. The method of claim 1, wherein the administering is by injection.

4. The method of claim 3, wherein the injection is intramyocardial.

5. The method of claim 3, wherein the injection is transepicardial.

6. The method of claim 1, wherein the administering is via a catheter.

7. The method of claim 1, wherein the adult cardiac stem cells differentiate into myocytes, smooth muscle cells, and endothelial cells.

8. The method of claim 7 wherein at least some of the differentiated adult cardiac stem cells assemble into myocardial tissue and myocardial vessels.

9. The method of claim 1, wherein said method also regenerates cardiac vessels.

10. The method of claim 1, wherein the at least one variant of hepatocyte growth factor is administered at varying concentrations of about 0.1 to about 400 ng/ml at different places of administration.

11. The method of claim 10, wherein the varying concentrations of the at least one variant of hepatocyte growth factor increase progressively in a direction towards the damaged myocardium.

12. The method of claim 10 wherein said at least one variant of hepatocyte growth factor is administered at varying concentrations of about 50 to about 200 ng/ml at different places of administration.

13. The method of claim 1, further comprising administering a second cytokine, wherein the second cytokine induces proliferation of adult cardiac stem cells.

14. The method of claim 13, wherein the second cytokine is insulin-like growth factor-1.

15. The method of claim 14, wherein the insulin-like growth factor-1 is administered at a concentration from about 0.1 ng/ml to about 500 ng/ml.

16. The method of claim 15, wherein the insulin-like growth factor-1 is administered at a concentration from about 150 ng/ml to about 250 ng/ml.

17. The method of claim 16, wherein the insulin-like growth factor-1 is administered at a concentration of about 200 ng/ml.

18. The method of claim 1, wherein said variant of hepatocyte growth factor is HP11.

19. The method of claim 1, wherein said variant of hepatocyte growth factor is HP21.

20. A method for restoring functional and structural integrity to damaged myocardium in a subject in need thereof, the method comprising administering to the subject an effective amount of at least one variant of hepatocyte growth factor selected from the group consisting of NK1, 1K1, 1K2, HP11, HP12, and HP21 to form a chemotactic gradient in the subject's heart sufficient to cause adult cardiac stem cells resident in the heart to replicate and migrate to the area of the damaged myocardium, wherein said gradient is formed by multiple injections of said at least one variant of hepatocyte growth factor from storage areas of said resident adult cardiac stem cells to a border zone of the damaged myocardium, and wherein the functional and structural integrity of the damaged myocardium is restored following the migration of adult cardiac stem cells to the area of damaged myocardium.

21. The method of claim 20, wherein the multiple injections comprise variable concentrations of said variant of hepatocyte growth factor.

22. The method of claim 20, wherein the storage areas of said resident adult cardiac stem cells are one or more of the subject's myocardial apex, left atrium, and right atrium.

23. The method of claim 20, wherein at least two of the injections are done at opposite sides of the border zone.

24. The method of claim 20, further comprising administering a second cytokine, wherein the second cytokine induces proliferation of adult cardiac stem cells.

25. The method of claim 24, wherein the second cytokine is insulin-like growth factor-1.

26. The method of claim 20, wherein said variant of hepatocyte growth factor is HP11.

27. The method of claim 20, wherein said variant of hepatocyte growth factor is HP21.

* * * * *

SEQUENCE LISTING

```
<160> NUMBER OF SEQ ID NOS: 5

<210> SEQ ID NO 1
<211> LENGTH: 728
<212> TYPE: PRT
<213> ORGANISM: Homo sapiens

<400> SEQUENCE: 1

Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190
```

```
Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Ala His
        435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605
```

```
Lys Thr Ser Cys Ser Val Tyr Gly Trp Gly Tyr Thr Gly Leu Ile Asn
            610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                    645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
                675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 2
<211> LENGTH: 728
<212> TYPE: PRT
<213> ORGANISM: Homo sapiens

<400> SEQUENCE: 2

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Glu Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                    100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                    180                 185                 190

Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
        210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255
```

```
Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685
```

```
Gly Val Ile Val Pro Gly Arg Gly Cys Ala Ile Pro Asn Arg Pro Gly
    690             695             700

Ile Phe Val Arg Val Ala Tyr Tyr Ala Lys Trp Ile His Lys Ile Ile
705             710             715             720

Leu Thr Tyr Lys Val Pro Gln Ser
            725

<210> SEQ ID NO 3
<211> LENGTH: 728
<212> TYPE: PRT
<213> ORGANISM: Homo sapiens

<400> SEQUENCE: 3

Met Trp Val Thr Lys Leu Leu Pro Ala Leu Leu Gln His Val Leu
1               5                   10                  15

Leu His Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Glu Cys Thr Glu Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335
```

-continued

```
His Asp Met Thr Pro Glu Asn Phe Lys Cys Lys Asp Leu Arg Glu Asn
            340                 345                 350
Tyr Cys Arg Asn Pro Asp Gly Ser Glu Ser Pro Trp Cys Phe Thr Thr
        355                 360                 365
Asp Pro Asn Ile Arg Val Gly Tyr Cys Ser Gln Ile Pro Asn Cys Asp
    370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Ala His
        435                 440                 445
Gly Pro Trp Cys Tyr Thr Gly Asn Pro Leu Ile Pro Trp Asp Tyr Cys
    450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
        515                 520                 525
Val Leu Thr Ala Arg Gln Cys Phe Pro Ser Arg Asp Leu Lys Asp Tyr
    530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
        595                 600                 605
Lys Thr Ser Cys Ser Val Tyr Gly Trp Gly Tyr Thr Gly Leu Ile Asn
    610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
            660                 665                 670
Tyr Gly Gly Pro Leu Val Cys Glu Gln His Lys Met Arg Met Val Leu
        675                 680                 685
Gly Val Ile Val Pro Gly Arg Gly Cys Ala Ile Pro Asn Arg Pro Gly
    690                 695                 700
Ile Phe Val Arg Val Ala Tyr Tyr Ala Lys Trp Ile His Lys Ile Ile
705                 710                 715                 720
Leu Thr Tyr Lys Val Pro Gln Ser
                725

<210> SEQ ID NO 4
<211> LENGTH: 183
<212> TYPE: PRT
<213> ORGANISM: Homo sapiens
<400> SEQUENCE: 4
```

-continued

```
Tyr Ala Glu Gly Gln Arg Lys Arg Arg Asn Thr Ile His Glu Phe Lys
  1               5                  10                  15

Lys Ser Ala Lys Thr Thr Leu Ile Lys Ile Asp Pro Ala Leu Lys Ile
             20                  25                  30

Lys Thr Lys Lys Val Asn Thr Ala Asp Gln Cys Ala Asn Arg Cys Thr
         35                  40                  45

Arg Asn Lys Gly Leu Pro Phe Thr Cys Lys Ala Phe Val Phe Asp Lys
     50                  55                  60

Ala Arg Lys Gln Cys Leu Trp Phe Pro Phe Asn Ser Met Ser Ser Gly
 65                  70                  75                  80

Val Lys Lys Glu Phe Gly His Glu Phe Asp Leu Tyr Glu Asn Lys Asp
                 85                  90                  95

Tyr Ile Arg Asn Cys Ile Ile Gly Lys Gly Arg Ser Tyr Lys Gly Thr
            100                 105                 110

Val Ser Ile Thr Lys Ser Gly Ile Lys Cys Gln Pro Trp Ser Ser Met
        115                 120                 125

Ile Pro His Glu His Ser Phe Leu Pro Ser Ser Tyr Arg Gly Lys Asp
    130                 135                 140

Leu Gln Glu Asn Tyr Cys Arg Asn Pro Arg Gly Glu Glu Gly Gly Pro
145                 150                 155                 160

Trp Cys Phe Thr Ser Asn Pro Glu Val Arg Tyr Glu Val Cys Asp Ile
                165                 170                 175

Pro Gln Cys Ser Glu Val Glu
            180
```

<210> SEQ ID NO 5
<211> LENGTH: 183
<212> TYPE: PRT
<213> ORGANISM: Homo sapiens

<400> SEQUENCE: 5

```
Tyr Ala Glu Gly Gln Arg Lys Arg Arg Asn Thr Ile His Glu Phe Lys
  1               5                  10                  15

Lys Ser Ala Lys Thr Thr Leu Ile Lys Ile Asp Pro Ala Leu Lys Ile
             20                  25                  30

Lys Thr Lys Lys Val Asn Thr Ala Asp Gln Cys Ala Asn Arg Cys Thr
         35                  40                  45

Arg Asn Lys Gly Leu Pro Phe Thr Cys Lys Ala Phe Val Phe Asp Lys
     50                  55                  60

Ala Arg Lys Gln Cys Leu Trp Phe Pro Phe Asn Ser Met Ser Ser Gly
 65                  70                  75                  80

Val Lys Lys Glu Phe Gly His Glu Phe Asp Leu Tyr Glu Asn Lys Asp
                 85                  90                  95

Tyr Ile Arg Asn Cys Ile Ile Gly Glu Gly Glu Ser Tyr Lys Gly Thr
            100                 105                 110

Val Ser Ile Thr Lys Ser Gly Ile Lys Cys Gln Pro Trp Ser Ser Met
        115                 120                 125

Ile Pro His Glu His Ser Phe Leu Pro Ser Ser Tyr Arg Gly Lys Asp
    130                 135                 140

Leu Gln Glu Asn Tyr Cys Arg Asn Pro Arg Gly Glu Glu Gly Gly Pro
145                 150                 155                 160

Trp Cys Phe Thr Ser Asn Pro Glu Val Arg Tyr Glu Val Cys Asp Ile
                165                 170                 175

Pro Gln Cys Ser Glu Val Glu
            180
```